(12) United States Patent
Kim et al.

(10) Patent No.: US 9,924,880 B2
(45) Date of Patent: Mar. 27, 2018

(54) RF DOPPLER BIO-SIGNAL SENSOR FOR CONTINUOUS HEART RATE VARIABILITY AND BLOOD PRESSURE MONITORING

(71) Applicant: Samsung Electronics Co., Ltd., Suwon-si, Gyeonggi-do (KR)

(72) Inventors: Insoo Kim, Mountain View, CA (US); Daquan Huang, Mountain View, CA (US); Jungsuek Oh, Mountain View, CA (US); Yusuf A. Bhagat, Mountain View, CA (US); Sean D. Lai, Mountain View, CA (US); Johnny T. Homer, Mountain View, CA (US)

(73) Assignee: Samsung Electronics Co., Ltd., Suwon-Si (KR)

( * ) Notice: Subject to any disclaimer, the term of this patent is extended or adjusted under 35 U.S.C. 154(b) by 19 days.

(21) Appl. No.: 14/988,629

(22) Filed: Jan. 5, 2016

(65) Prior Publication Data

US 2016/0228010 A1    Aug. 11, 2016

Related U.S. Application Data

(60) Provisional application No. 62/114,804, filed on Feb. 11, 2015, provisional application No. 62/243,321, filed on Oct. 19, 2015.

(51) Int. Cl.
| | |
|---|---|
| *A61B 5/021* | (2006.01) |
| *H04Q 9/00* | (2006.01) |
| *A61B 5/00* | (2006.01) |
| *A61B 5/05* | (2006.01) |
| *A61B 5/0285* | (2006.01) |

(52) U.S. Cl.
CPC ............ *A61B 5/021* (2013.01); *A61B 5/0285* (2013.01); *A61B 5/0507* (2013.01); *A61B 5/681* (2013.01); *H04Q 9/00* (2013.01); *A61B 5/0015* (2013.01); *H04Q 2209/50* (2013.01); *H04Q 2209/84* (2013.01)

(58) Field of Classification Search
CPC ..... A61B 5/0285; A61B 5/0507; A61B 5/681; A61B 5/021; H04Q 9/00; G01S 13/02; G01S 13/06; G01S 13/42
USPC ...................................................... 340/870.07
See application file for complete search history.

(56) References Cited

U.S. PATENT DOCUMENTS

| | | |
|---|---|---|
| 4,187,501 A * | 2/1980 | Olesch .................... G01S 13/56 333/240 |
| 4,513,748 A | 4/1985 | Nowogrodzki et al. |
| 7,753,849 B2 | 7/2010 | Morgan et al. |

(Continued)

*Primary Examiner* — Qutbuddin Ghulamali

(57) ABSTRACT

A method implemented by a device to measure a bodily parameter includes transmitting, by a transmit (Tx) antenna of an antenna pair, a first radar pulse to a receive (Rx) antenna of the antenna pair. The method also includes receiving, by the receive (Rx) antenna, the first radar pulse. The first radar pulse travels through a radar target between the Tx antenna and the Rx antenna. The method further includes transmitting, by the Tx antenna, a second radar pulse to the Rx antenna. In addition the method includes receiving, by the Rx antenna, the second radar pulse, wherein the second radar pulse travels through the radar target between the Tx antenna and the Rx antenna. The method also includes determining a bodily parameter within the radar target as a function of the transmission and the reception of the first radar pulse and the second radar pulse.

12 Claims, 17 Drawing Sheets

(56) References Cited

U.S. PATENT DOCUMENTS

| | | |
|---|---|---|
| 8,750,971 B2 | 6/2014 | Tran |
| 9,445,729 B2 * | 9/2016 | McMahon ............ A61B 5/4836 |
| 9,526,437 B2 * | 12/2016 | Tupin, Jr. ............. A01K 27/009 |
| 2008/0119716 A1 | 5/2008 | Boric-Lubecke et al. |
| 2010/0026550 A1 * | 2/2010 | Rosenbury ......... A61B 5/02438 |
| | | 342/22 |
| 2010/0286533 A1 | 11/2010 | Lee et al. |
| 2014/0024917 A1 * | 1/2014 | McMahon ............ A61B 5/4836 |
| | | 600/407 |
| 2014/0235965 A1 | 8/2014 | Tran |
| 2015/0359463 A1 * | 12/2015 | Matthews .............. A61B 5/024 |
| | | 600/407 |

* cited by examiner

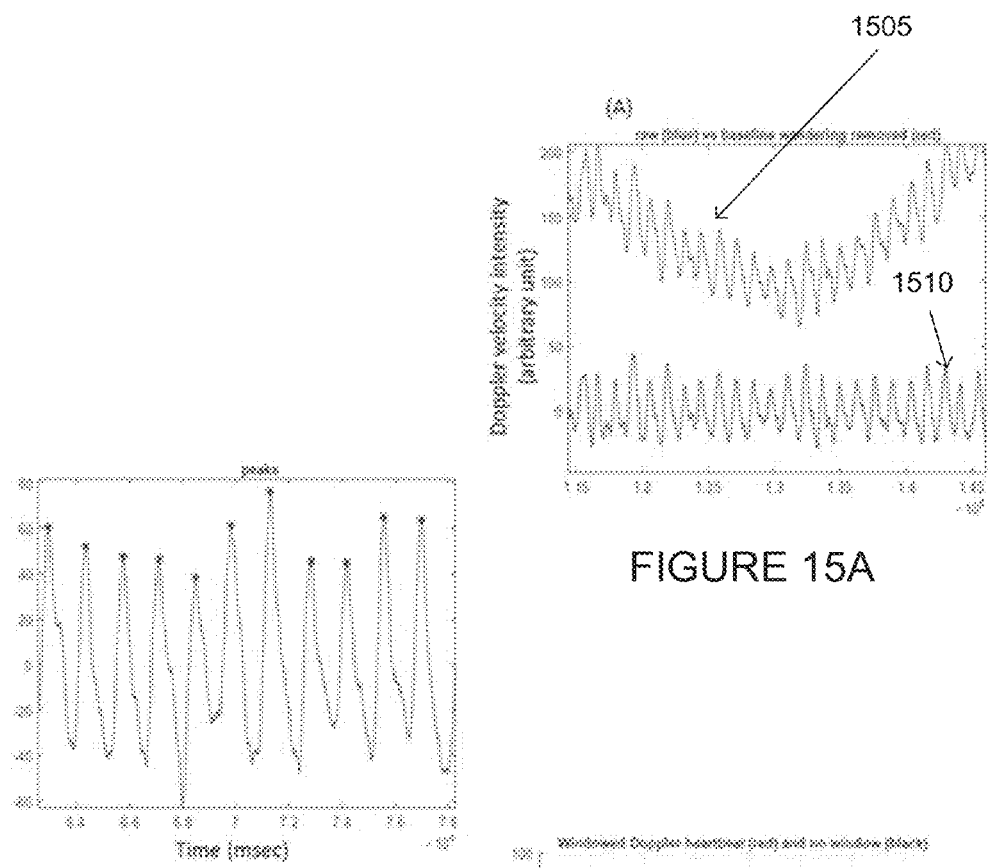
FIGURE 15A
FIGURE 15B
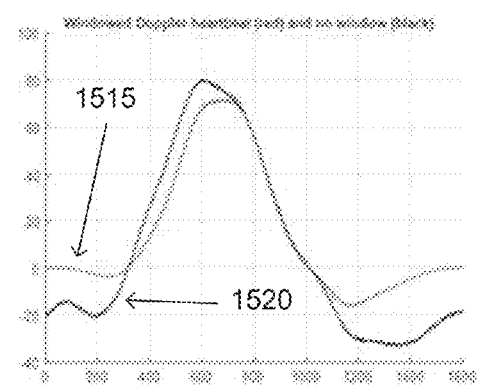
FIGURE 15C

RF DOPPLER BIO-SIGNAL SENSOR FOR CONTINUOUS HEART RATE VARIABILITY AND BLOOD PRESSURE MONITORING

CROSS-REFERENCE TO RELATED APPLICATION(S) AND CLAIM OF PRIORITY

The present application claims priority to U.S. Provisional Patent Application Ser. No. 62/114,804, filed Feb. 11, 2015, entitled "RF DOPPLER BIO-SIGNAL SENSOR FOR PERSONAL HEALTH MONITORING" and to U.S. Provisional Patent Application Ser. No. 62/243,321, filed Oct. 19, 2015 entitled "DOPPLER SYSTEMS AND APPARATUS FOR CUFFLESS CONTINUOUS BLOOD PRESSURE MONITORING." The content of the above-identified patent documents is incorporated herein by reference in its entirety.

TECHNICAL FIELD

The present application relates generally to monitoring bodily parameters and, more specifically, to a monitoring bodily parameters using a mobile electronic device.

BACKGROUND

Some cuff devices for blood pressure monitoring can be ill-suited for measuring health parameters, for example due to their bulkiness and the like. Some cuff-less blood pressure devices involve electrical sensors, requiring two points of contact that can be difficult to implement with mobile devices, and can require tight contact with the prepared skin area under interrogation. Neither existing technology categories provide continuous blood pressure information.

SUMMARY

A device to measure a bodily parameter is provided. The device includes an antenna pair including a transmit (Tx) antenna configured to transmit one or more radar pulses and a receive (Rx) antenna configured to receive the one or more radar pulses. The Tx antenna and the Rx antenna are positioned so that a radar target can be positioned between the Tx antenna and the Rx antenna. The device also includes a processor. The processor is configured to control the Tx antenna to transmit a first radar pulse and a second radar pulse. The processor is also configured to control the Rx antenna to receive the first radar pulse and the second radar pulse. The first radar pulse and the second radar pulse travel through the radar target. The processor is further configured to determine a bodily parameter within the radar target as a function of the transmission and the reception of the first radar pulse and the second radar pulse.

A device to measure a bodily parameter is provided. The device includes an antenna pair including a transmit (Tx) antenna configured to transmit one or more radar pulses and a receive (Rx) antenna configured to receive the one or more radar pulses. The Rx antenna is positioned to receive the one or more radar pulses transmitted from the Tx antenna and reflected off of a radar target. The device also includes a processor. The processor is configured to control the Tx antenna to transmit a first radar pulse and a second radar pulse. The processor is also configured to control the Rx antenna to receive the first radar pulse and the second radar pulse. The first radar pulse and the second radar pulse are reflected off of the radar target. The processor is further configured to determine a movement direction of the radar target relative to the antenna pair. In addition, the processor is configured to determine the bodily parameter within the radar target as a function of (1) the movement direction and (2) the transmission and the reception of the first radar pulse and the second radar pulse.

A method implemented by a device to measure a bodily parameter is provided. The method includes transmitting, by a transmit (Tx) antenna of an antenna pair, a first radar pulse to a receive (Rx) antenna of the antenna pair. The method also includes receiving, by the receive (Rx) antenna, the first radar pulse. The first radar pulse travels through a radar target between the Tx antenna and the Rx antenna. The method further includes transmitting, by the Tx antenna, a second radar pulse to the Rx antenna. In addition, the method includes receiving, by the Rx antenna, the second radar pulse. The second radar pulse travels through the radar target between the Tx antenna and the Rx antenna. The method also includes determining a bodily parameter within the radar target as a function of the transmission and the reception of the first radar pulse and the second radar pulse. The first radar pulse and the second radar pulse include a Doppler radar pulse.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 15A, 15B, and 15C illustrate example graphs to show how heart rate is calculated according to this disclosure;

DETAILED DESCRIPTION

Figure 1:
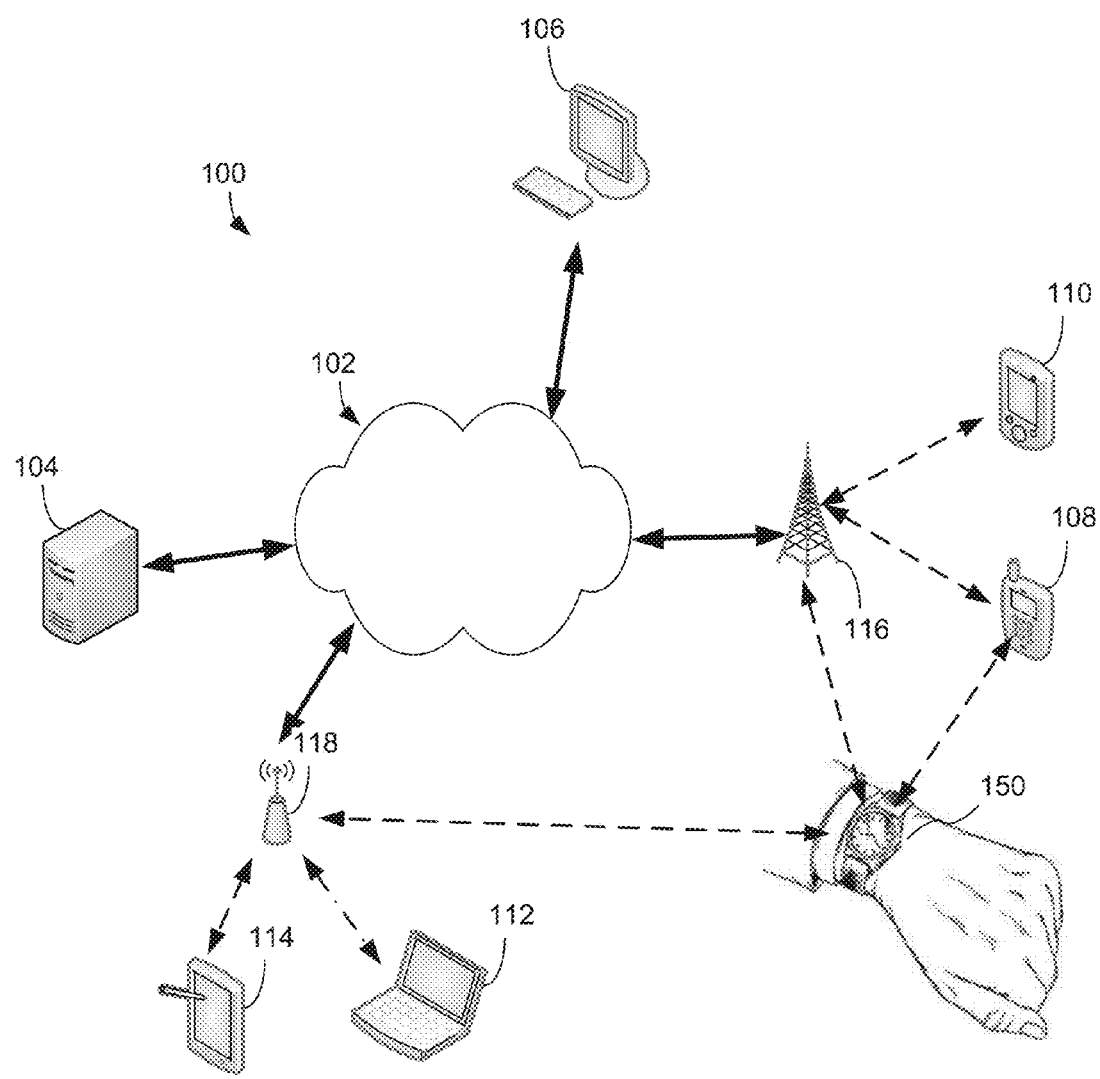
FIG. 1 illustrates an example communication system according to this disclosure.

FIGS. 1 through 17, discussed below, and the various embodiments used to describe the principles of the present invention in this patent document are by way of illustration only and should not be construed in any way to limit the scope of the disclosure. Those skilled in the art will understand that the principles of this disclosure may be implemented in any suitably arranged device or system.

The following documents and standards descriptions are hereby incorporated by reference into the present disclosure as if fully set forth herein: Preventing Chronic Disease. A Vital Investment, WHO Report, 2005 [1]; Global Status Report on Noncommunicable Diseases, World Health Organization, 2005 [2]; Projection of Chronic Illness and Cost Inflation, RAND Corporation 2005 [3]; James P A, Oparil S, Carter B L, Cushman W C, Dennison-Himmelfarb C, Handler J, Lackland D T, LeFevre M L, MacKenzie T D, Ogedegbe O, Smith S C Jr, Svetkey L P, Taler S J, Townsend R R, Wright J T Jr, Narva A S, Ortiz E., "2014 evidence-based guideline for the management of high blood pressure in adults: report from the panel members appointed to the Eighth Joint National Committee (JNC 8)" JAMA. 2014 Feb. 5; 311(5):507-520, May 2014 [4]; IEEE Standards for Wearable Cuffless Blood Pressure Monitoring Devices 1708-2014 [5]; Abildstrom S Z, Jensen B T, Agner E, Torp-Pedersen C, Nyvad O, Wachtell K, Ottensen M M, Kanters J K and Beat Study Group, "Heart Rate Variability in Risk Prediction after Myocardial Infarction", J Cardiovasc Electrophysiol, 14(2): 168-173, February 2003 [6]; Cohen H, Kotler M, Matar M A, Kaplan Z, Loewenthal U, Miodownik H and Cassuto Y, "Analysis of heart rate variability in posttraumatic stress disorder patients in response to trauma-related reminder", Biol Psychiatry, 44(10): 1054-1059, November 1998 [7]; McCarthy B M, O'Flynn B, Mathewson A, "An Investigation of Pulse Transit Time as a Noninvasive Blood Pressure Measurement Method", Journal of Physics, 307, 2011 [8]; and Beulen B W, Bijnens N, Koutsouridis G G, Brands P J, Rutten M C and Van de Vosse F N, "Toward noninvasive blood pressure assessment in arteries by using ultrasound", Ultrasound Med Biol, 37(5): 788-797, March 2011 [9].

As discussed herein, an RF Doppler-based sensor in a wrist-watch form factor for measuring heart rate variability and blood flow velocity to provide continuous estimates of cuff-less blood pressure is provided. Also, as discussed herein, a sequence of signal processing and intelligence algorithm chains for measuring blood pressure can be inferred continuously.

Elevated blood pressure (BP) is a critical risk factor for a host of cardiovascular diseases including hypertension [1]. Annually, 7.5 million deaths worldwide are attributed to elevated BP. BP levels positively correlate to risk for stroke and coronary heart disease. The risk of cardiovascular disease can double for each incremental increase of 20/10 mmHg BP [2, 3]. BP values depend on cardiac output, diameter of arteries, and the quantity of blood. Arterial pressure is commonly measured by a sphygmomanometer with BP varying for each heart beat between systolic (such as peak pressure in the arteries at the end of the cardiac cycle) and diastolic (such as minimum pressure in arteries near beginning of cardiac cycle). Normal measured values for resting adults are 120/80 mmHg.

Some non-continuous BP measurement methods pause between about 1 and 2 minutes to avoid measurement errors and typically yield unreliable measurements during irregular heartbeats (such as arrhythmias), and can be inaccurate during rapid pulse pressure changes or severe shock. Continuous BP monitoring can be used with the chronically ill suffering from hypertension, for cardiopulmonary fitness, for maintaining target BP levels during exercise, and for stroke detection where ischemic events are accompanied by rapid changes in BP [4]. Some noninvasive devices for ambulatory or home-based BP measurement are based on an oscillometric method which uses an inflatable cuff [5]. The cuff pressure can be intolerable to some individuals who need constant monitoring. Bruising under the inflating cuff and sleep disturbances are adverse effects associated with this approach. Subject motion can impair the accuracy of the measurements. Further, the cuff size is dependent on the upper arm circumference of users. These devices can be insufficient indicators of hypertension and yield poor information on the presence of arterial stiffness from vasculature [5].

Heart rate variability (HRV) refers to the normally occurring beat-to-beat changes in heart rate. HRV is vital for assessing function and balance of the autonomic nervous system and is a key indicator of age, stress level, cardiac health, well-being, and the like [6, 7]. Reductions in HRV correlate with increased stress and anxiety, respiratory arrhythmia, myocardial infarctions, and the like, and are commonly observed in smokers and in obese and hypertensive individuals.

HRV monitoring can be indicative of heart attacks, help gauge elevated stress and disorders related to sleep to name a few. Photoplethysmography (PPG) and electrocardiography (ECG) based sensors can be used to measure HRV. However, subject motion can impair PPG signal accuracy and ECG measurements are limited by their preclusion to continuous monitoring. Movement of the sensor can lead to wide deviations drowning out blood volume signals and can cause missed or false extra beat readings. Cold extremities (such as with Raynaud's disorder) can result in weak pulses and tight coupling of the sensor to skin can cut off circulation and flatten the pulse wave.

Challenges that are common to both, cuff-less BP and HRV sensors are sensitivity to subject motion limiting continuous monitoring, sensitivity to position and subject dependent differences in artery diameter, skin color and distance from measurement point to the heart.

FIG. 1 illustrates an example computing system 100 according to this disclosure. The embodiment of the computing system 100 shown in FIG. 1 is for illustration only. Other embodiments of the computing system 100 could be used without departing from the scope of this disclosure.

As shown in FIG. 1, the system 100 includes a network 102, which facilitates communication between various components in the system 100. For example, the network 102 may communicate Internet Protocol (IP) packets, frame relay frames, Asynchronous Transfer Mode (ATM) cells, or other information between network addresses. The network 102 may include one or more local area networks (LANs), metropolitan area networks (MANs), wide area networks (WANs), all or a portion of a global network such as the Internet, or any other communication system or systems at one or more locations.

The network 102 facilitates communications between at least one server 104 and various client devices 106, 108, 110, 112, 114, and 150. Each server 104 includes any suitable computing or processing device that can provide computing services for one or more client devices. Each server 104 could, for example, include one or more processing devices, one or more memories storing instructions and data, and one or more network interfaces facilitating communication over the network 102.

Each client device 106, 108, 110, 112, 114, and 150 represents any suitable computing or processing device that interacts with at least one server or other computing device(s) over the network 102. In this example, the client devices 106, 108, 110, 112, 114, and 150 include a desktop computer 106, a mobile telephone or smartphone 108, a personal digital assistant (PDA) 110, a laptop computer 112, a tablet computer 114, and a wearable electronic device 300. However, any other or additional client devices could be used in the computing system 100.

In this example, some client devices 106, 108, 110, 112, 114, and 150 communicate indirectly with the network 102. For example, the client devices 108, 110, and 150 communicate via one or more base stations 116, such as cellular base stations or eNodeBs. Also, the client devices 112, 114, and 150 communicate via one or more wireless access points 118, such as IEEE 802.11 wireless access points. Note that these are for illustration only and that each client device could communicate directly with the network 102 or indirectly with the network 102 via any suitable intermediate device(s) or network(s).

As described in more detail below, the client devices including the wearable electronic device 150 is used to measure bodily parameters such as blood velocity, blood pressure, heart rate, arterial shape, and the like. For example, the wearable electronic device 150 can communicate directly with another client device (such as client device 108) or can communicate indirectly with other client devices and the server 104 via a base station 116, an access point 118, or a client device (such as client device 108). As another example, the wearable electronic device 150 can output bodily parameters via an interface on the wearable electronic device 150 or via another client device. As yet another example, the wearable electronic device 150 can also transmit bodily parameters to the server 104 for data storage and to be accessed by an authorized party.

Although FIG. 1 illustrates one example of a computing system 100, various changes may be made to FIG. 1. For example, the system 100 could include any number of each component in any suitable arrangement. In general, computing and communication systems come in a wide variety of configurations, and FIG. 1 does not limit the scope of this disclosure to any particular configuration. While FIG. 1 illustrates one operational environment in which various features disclosed in this patent document can be used, these features could be used in any other suitable system.

Figure 2:
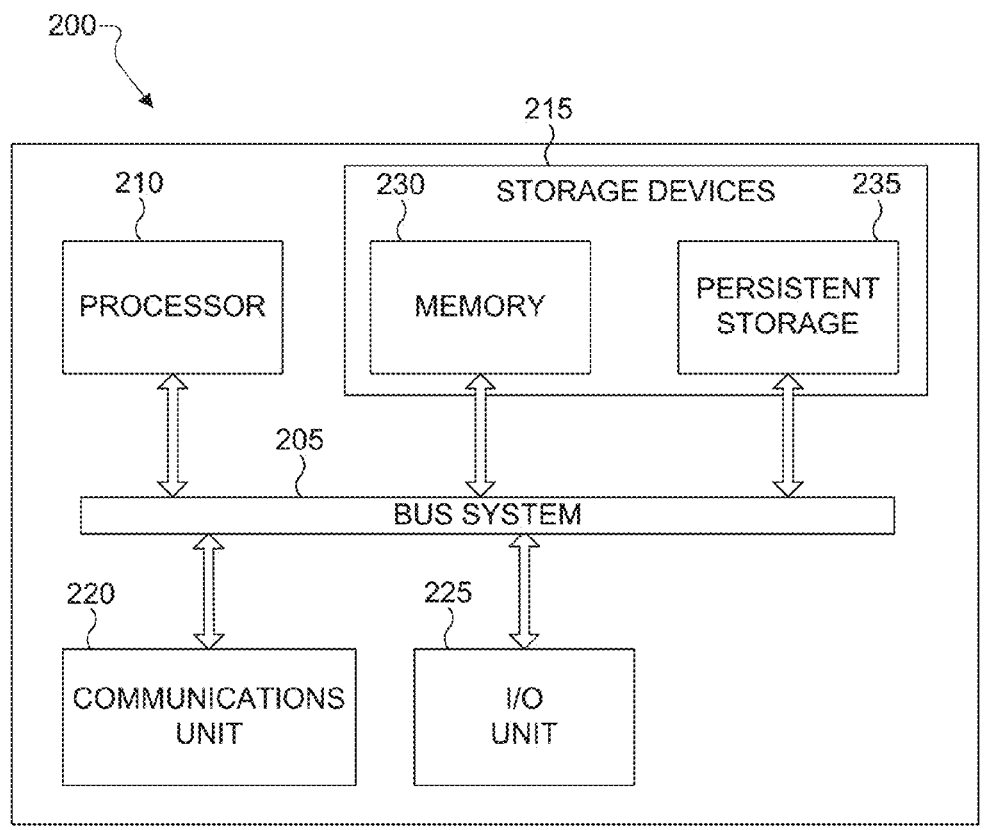
FIGS. 2 and 3 illustrate example devices in a communication system according to this disclosure.
Figure 3:
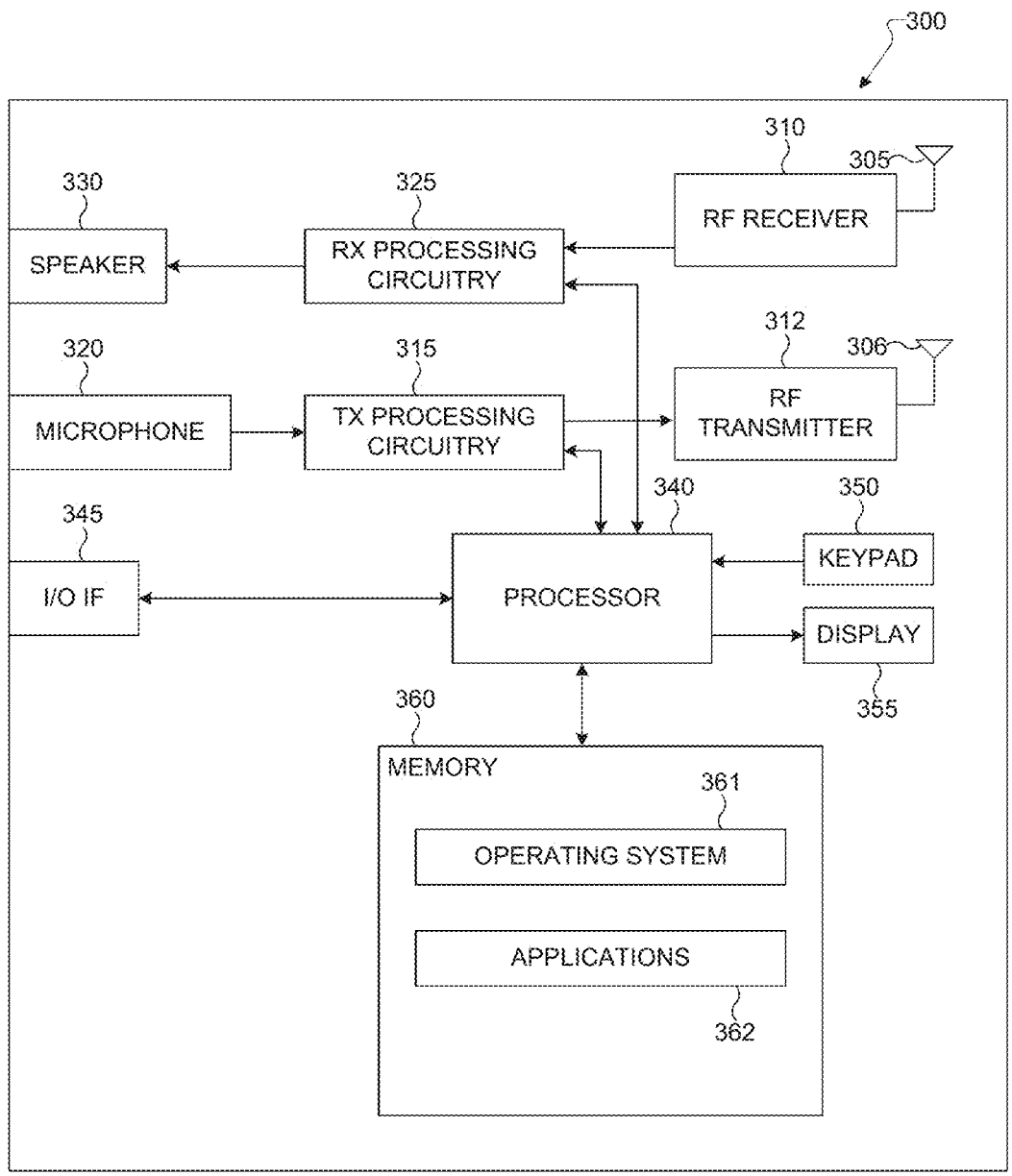

FIGS. 2 and 3 illustrate example devices in a communication system according to this disclosure. In particular, FIG. 2 illustrates an example server 200, and FIG. 3 illustrates an example client device 300. The server 200 could represent the server 104 in FIG. 1, and the client device 300 could represent one or more of the client devices 106, 108, 110, 112, 114, or 150 in FIG. 1.

As shown in FIG. 2, the server 200 includes a bus system 205, which supports communication between at least one processor 210, at least one storage device 215, at least one communications unit 220, and at least one input/output (I/O) unit 225.

The processor 210 executes instructions that may be loaded into a memory 230. The processor 210 may include any suitable number(s) and type(s) of processors or other devices in any suitable arrangement. Example types of processors 210 include microprocessors, microcontrollers, digital signal processors, field programmable gate arrays, application specific integrated circuits, and discreet circuitry.

The memory 230 and a persistent storage 235 are examples of storage devices 215, which represent any structure(s) capable of storing and facilitating retrieval of information (such as data, program code, and/or other suitable information on a temporary or permanent basis). The memory 230 may represent a random access memory or any other suitable volatile or non-volatile storage device(s). The persistent storage 235 may contain one or more components or devices supporting longer-term storage of data, such as a ROM, hard drive, Flash memory, or optical disc.

The communications unit 220 supports communications with other systems or devices. For example, the communications unit 220 could include a network interface card or a wireless transceiver facilitating communications over the network 102. The communications unit 220 may support communications through any suitable physical or wireless communication link(s).

The I/O unit 225 allows for input and output of data. For example, the I/O unit 225 may provide a connection for user input through a keyboard, mouse, keypad, touchscreen, or other suitable input device. The I/O unit 225 may also send output to a display, printer, or other suitable output device.

Note that while FIG. 2 is described as representing the server 104 of FIG. 1, the same or similar structure could be used in one or more of the client devices 106, 108, 110, 112, 114, and 150. For example, a laptop or desktop computer could have the same or similar structure as that shown in FIG. 2.

As shown in FIG. 3, the client device 300 includes an antenna 305, a radio frequency (RF) receiver 310, an RF transmitter 312, transmit (TX) processing circuitry 315, a microphone 320, and receive (RX) processing circuitry 325. The client device 300 also includes a speaker 330, a processor 340, an input/output (I/O) interface (IF) 345, a keypad 350, a display 355, and a memory 360. The memory 360 includes an operating system (OS) program 361 and one or more applications 362.

The RF receiver 310 receives, from the antenna 305, an incoming RF signal transmitted by another component in a system. The RF receiver 310 down-converts the incoming RF signal to generate an intermediate frequency or baseband signal. The intermediate frequency or baseband signal is sent to the RX processing circuitry 325, which generates a processed baseband signal by filtering, decoding, and/or digitizing the baseband or IF signal. The RX processing circuitry 325 transmits the processed baseband signal to the speaker 330 (such as for voice data) or to the processor 340 for further processing (such as for web browsing data or for calculating bodily parameters based on the received RF signal).

The TX processing circuitry 315 receives analog or digital voice data from the microphone 320 or other outgoing baseband data (such as web data, e-mail, or interactive video game data, or a command to measure a bodily parameter) from the processor 340. The TX processing circuitry 315 encodes, multiplexes, and/or digitizes the outgoing baseband data to generate a processed baseband or intermediate frequency signal. The RF transmitter 312 receives the outgoing processed baseband or intermediate frequency signal from the TX processing circuitry 315 and up-converts the baseband or intermediate frequency signal to an RF signal that is transmitted via the antenna 306. In an embodiment, the two or more network access interfaces can include one or more I/O IFs 345, one or more RF receivers 310, one or more RF transmitters 312, or the like. The I/O IF 345 can communicate via a wired connection such as a network interface card for an Ethernet connection or a cable interface for a set top box. The RF receiver 310 can communicate with a wireless access point (such as wireless access points 118 or 119), a base station (such as base stations 116 or 117), the RF transmitter 312, or the like. The RF transmitter 312 can communicate with a wireless access point (such as wireless access points 118 or 119), a base station (such as base stations 116 or 117), the RF receiver 310, or the like.

The processor 340 can include one or more processors or other processing devices and execute the OS program 361 stored in the memory 360 in order to control the overall operation of the client device 300. For example, the processor 340 could control the reception of forward channel signals and the transmission of reverse channel signals by the RF receiver 310, the RF receiver, the RX processing circuitry 325, and the TX processing circuitry 315 in accordance with well-known principles. In some embodiments, the processor 340 includes at least one microprocessor or microcontroller.

The processor 340 is also capable of executing other processes and programs resident in the memory 360. The processor 340 can move data into or out of the memory 360 as required by an executing process. In some embodiments, the processor 340 is configured to execute the applications 362 based on the OS program 361 or in response to signals received from external devices or an operator. The processor 340 is also coupled to the I/O interface 345, which provides the client device 300 with the ability to connect to other devices such as laptop computers and handheld computers. The I/O interface 345 is the communication path between these accessories and the processor 340.

The processor 340 is also coupled to the keypad 350 and the display unit 355. The operator of the client device 300 can use the keypad 350 to enter data into the client device 300. The display 355 may be a liquid crystal display or other display capable of rendering text and/or at least limited graphics, such as from web sites.

The memory 360 is coupled to the processor 340. Part of the memory 360 could include RAM, and another part of the memory 360 could include a Flash memory or other ROM.

As described in more detail below, the client device 300 is configured to transmit an RF signal to a target such a region of a body of a living animal or human. The client device 300 is also configured to receive the transmitted RF signal (such as the RF signal transmitted from the RF transmitter 306) in order to determine a bodily parameter. The client device can include a wristwatch, armband, torso-band, one or more patches, or the like.

Although FIGS. 2 and 3 illustrate examples of devices in a communication system, various changes may be made to FIGS. 2 and 3. For example, various components in FIGS. 2 and 3 could be combined, further subdivided, or omitted and additional components could be added according to particular needs. As a particular example, the processor 340 could be divided into multiple processors, such as one or more central processing units (CPUs) and one or more graphics processing units (GPUs). Also, while FIG. 3 illustrates the client device 300 configured as a mobile telephone or smartphone, client devices could be configured to operate as other types of mobile or stationary devices. In addition, as with computing and communication networks, client devices and servers can come in a wide variety of configurations, and FIGS. 2 and 3 do not limit this disclosure to any particular client device or server.

Some cuff-less blood pressure sensors are based on five principles, namely, pulse wave analysis (PWA), pulse transit time (PTT) estimation, particle image velocimetry (NV), photo-acoustic and ultrasound based methods. In PWA, optical measurements such as tonometry permit recording of radial and carotid pressure waveforms. Through analysis of the waveform due to forward and reflective wave fronts, parameters relaying cardiovascular functional information can be extracted. PTT-based estimation involves the use of two sources related to the cardiac cycle, usually ECG and PPG to measure velocity [8]. Pulse wave velocity (PWV) is the rate at which aortic pressure waves travel. PWV is inversely proportional to PTT and is given by, $$PWV = L/PTT$$

where L is the distance the pulse has to travel between two arterial locations measuring the velocity. PWV is conventionally determined from the ECG-R wave and a cuff. PWV depends on elasticity, E, arterial thickness, t, arterial diameter, d, and density of the blood, p. The relationship is given by the Moens-Kortwegg equation.

$$PWV = \sqrt{\frac{gtE}{\rho d}}$$

where g is the gravitational constant (g can be omitted as pressure is assumed to be hydrostatic). The elastic modulus of the vessel increases exponentially with increasing BP such that $$E = E_0 e^{\gamma P}$$

where $E_0$ is the elastic modulus at zero pressure, P is the blood pressure (mmHg) and γ is a coefficient ranging from 0.016 to 0.018 (mmHg$^{-1}$).

The end point BP ($P_e$) can be related to PTT directly by (using some manipulation)

$$P_e = P_b - \frac{2}{\gamma PTT_b} \Delta PTT$$

where $P_b$ is the base blood pressure level, $PTT_b$ is the value of PTT corresponding to the pressure, $P_b$, while $\Delta PTT$ is the change in the PTT.

Several algorithms have been developed to estimate PWV. However, a consensus on a gold standard algorithm has not been reached. The method can include a calibration for improved accuracy since parameters accounting for vessel length and diameter may not be measured.

PIV characterizes the flow field in fluid dynamics. The particle-seeded can be illuminated with a light sheet generated by a pulsed laser. The particle patterns in the field are tracked frame by frame and the displacement data are converted to velocity using small time intervals between the illuminating laser pulses. The photo-acoustic approach can involve noninvasive high-resolution (such as about 10 μm) measurements of blood dynamics. Some studies using phantoms have shown the potential of estimating blood velocity with high accuracy. Ultrasound methods although well-established for flow measurements and indirectly for blood pressure estimation, can use a gel application that increases the operation time and can lead to a barrier in user convenience.

Beulen et al. [9] measured local pressure waveforms using ultrasound. They undertook a simultaneous estimation of distension waveforms and velocity profiles from a single noninvasive perpendicular ultrasound B-mode measurement. Velocity vectors were determined and local PWV was computed from the ratio between changes in flow and changes in cross-sectional vessel area. Further, accurate beat-to-beat pressure estimation for large arteries was also obtained. The drawbacks of this approach were that a one-time calibration may be needed with a cuff-type BP device. Also, the relationship between PWV and BP was not fully validated.

Figure 4:
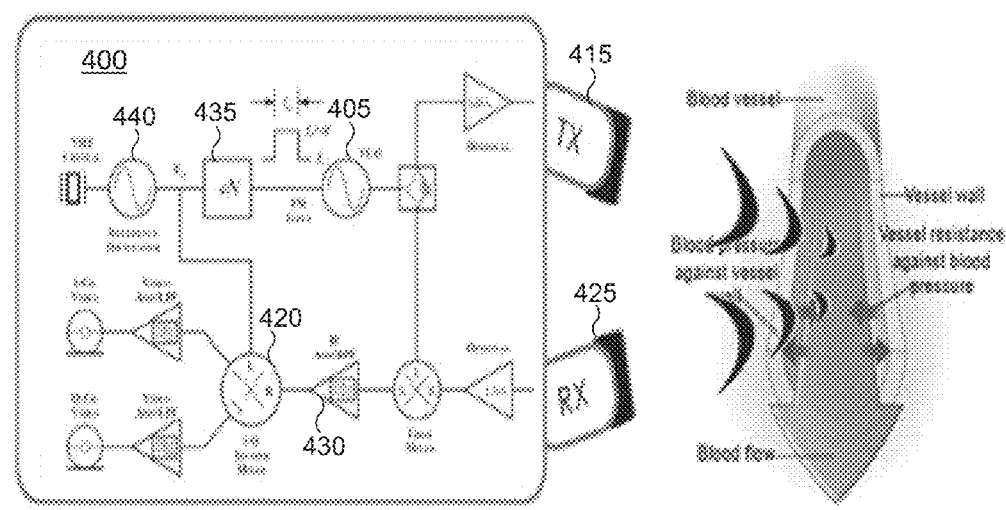
FIG. 4 illustrates an example system diagram of a pulse wave Doppler radar transceiver according to this disclosure.

FIG. 4 illustrates an example system diagram of a pulse wave Doppler radar transceiver 400 according to this disclosure. A pulsed radar transceiver 400 includes of a waveform generator 405 configured to generate a pulse waveform. The transmitter modulates this waveform to the RF and amplifies the waveform to a useful power level. The transmitter output is routed to the antenna 415 through a T/R switch 420. Returning echoes are routed again by the T/R switch 420 into the receiver via the antenna 425 based on a superheterodyne design. The first stage in such a monostatic radar system is a low noise RF amplifier 430. The first stage is followed by one or more stages of modulation of the received signal to successively lower the intermediate frequencies (IF) and to baseband where the signal is not modulated on to any carrier frequency. Each modulation is carried out with a mixer 435 and a local oscillator (LO) 440. Next, the baseband signal is sent to the signal processor. The signal processor performs some or all of a variety of functions such as pulse compression, matched filtering, Doppler filtering, integration, and the like. The output of the signal processor can take the form of a stream of detections with a measured range and angle coordinates.

A low power pulsed wave Doppler radar transceiver (Tx-Rx) 400 will enable detection of the frequency/phase shift of the returned signal and thereby enable a calculation of the velocity of the target material (such as blood). As the reflector moves between each transmit pulse, the returned signal has a phase difference or phase shift from pulse to pulse. This permits direct measurements of the blood velocity and arterial shape thereby permitting an estimation of heart rate (HR) and blood pressure.

Figure 5:
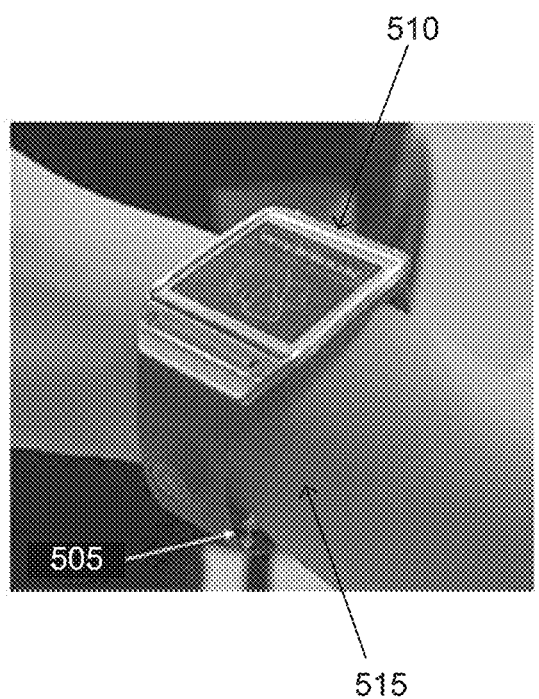
FIG. 5 illustrates an example gap between a wrist and a device according to this disclosure.
Figure 6:
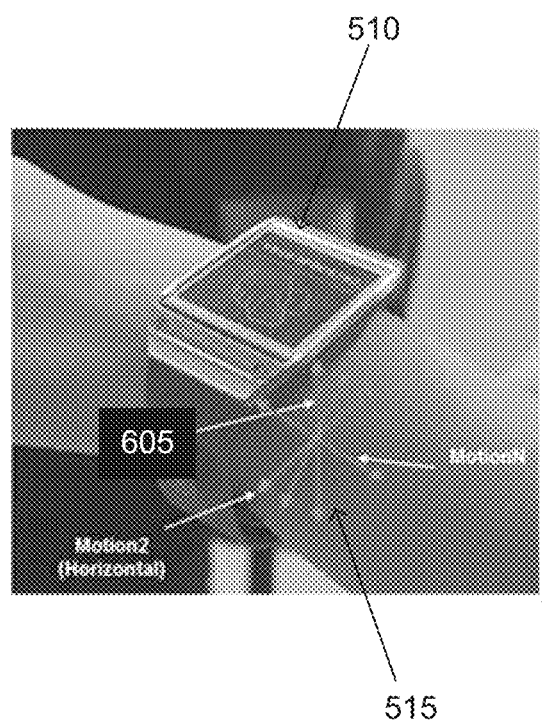
FIG. 6 illustrates an example movement of a wrist and a device according to this disclosure.
Figure 7A:
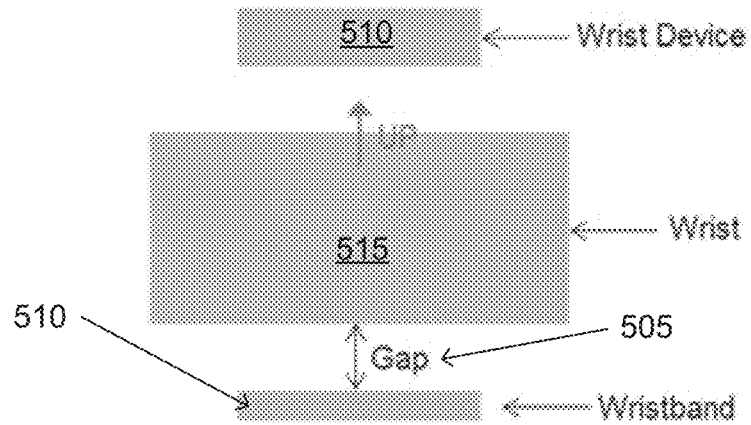
FIGS. 7A and 7B illustrate example motions between a wrist and a wrist device according to this disclosure.
Figure 7B:
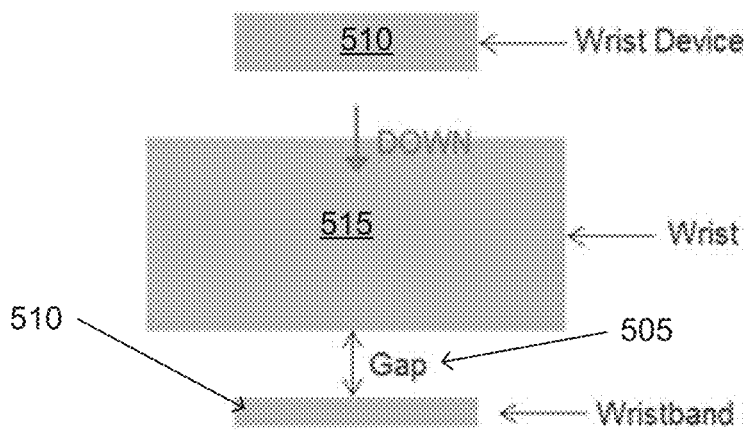

Wireless signals emitted by wearable devices are affected by continuous human motion such as jogging. This can be a critical problem for wrist devices accompanied by a gap 505 between the devices 510 and the wrist 515 as shown in FIG. 5. The millimeter wave heart rate monitoring (HRM) system as discussed herein can address this problem. An antenna configuration in this invention can improve the stability of the frequency response of the HRM system discussed herein. The frequency response is depicted by analyzing Doppler effects (or shifts) caused by undesired human motion. FIG. 6 illustrates possible human motion applied on wrist devices. In order to simplify problem analysis, motion1 605 drawing vertical trace is selected as shown in FIGS. 7A and 7B. The vertical motion consists of two sub-motions: (1) when the wrist moves up as illustrated in FIG. 7A; and (2) when the wrist moves down as shown in FIG. 7B.

Figure 8A:
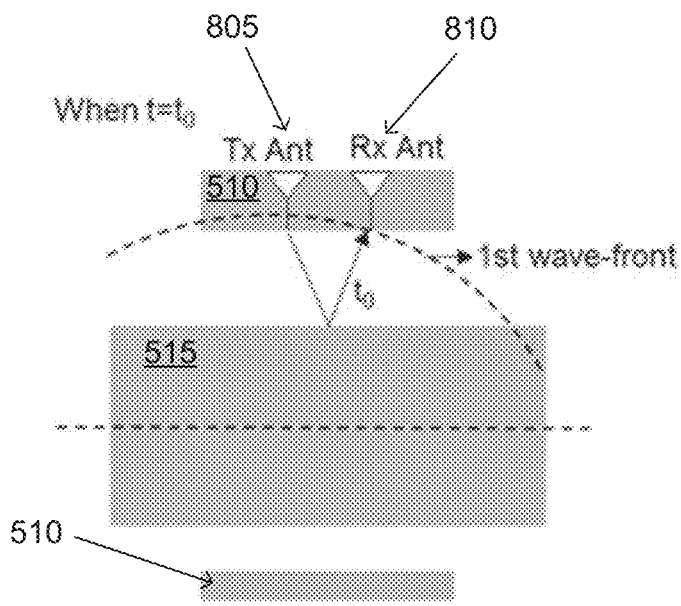
FIGS. 8A and 8B illustrate an example monostatic sensor configuration according to this disclosure.
Figure 8B:
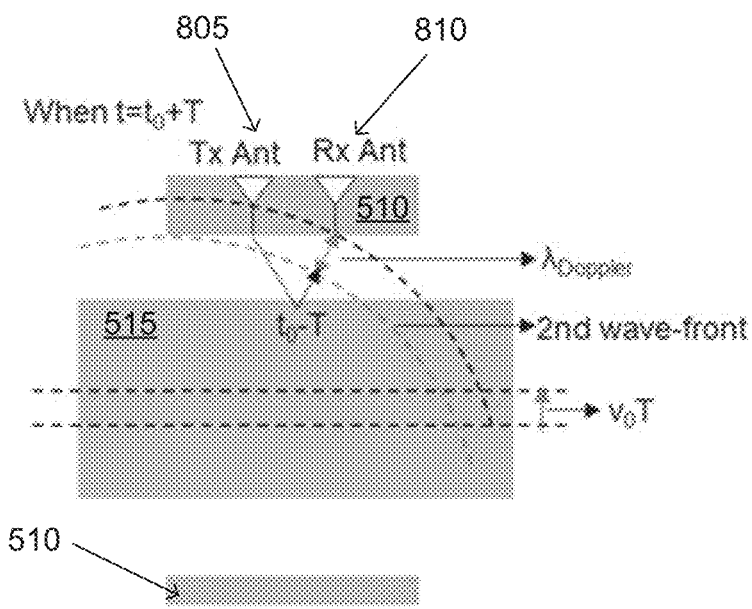

FIGS. 8A and 8B illustrate an example monostatic sensor configuration according to this disclosure. Monostatic radar includes a transmitter 805 to be collocated with the receiver 810 or both the transmitter 805 and the receiver 810 share the same functions. The most common antenna arrangement in on-body devices could be to place Tx antenna(s) 805 and Rx antenna(s) 810 close to each other, rendering a monostatic sensor configuration as shown in FIGS. 8A and 8B. As shown in FIG. 8A, a first signal is transmitted from the Tx antenna 805 at t=0, the first wave front arrives at the Rx antenna 810 at t=$t_0$. As shown in FIG. 8B, a second signal is transmitted from the Tx antenna 805 at t=T and a human arm (including the wrist 515) moves up with the velocity of $v_0$ between t=$t_0$ and t=$t_0$+T. The distance between the first wave front and the second wave front is one wavelength at Doppler frequency. In other words, with a monostatic Tx/Rx antenna configuration as shown in FIG. 8A when t=$t_0$ (first signal is transmitted from the Tx antenna 805 at t=0 and arrives the Rx antenna 810 at t=$t_0$) and as shown in FIG. 8B a second signal is transmitted at t=T (T=$\lambda_0$/c where c is light speed) and human arm moves up with the velocity of $v_0$ between t=$t_0$ and t=$t_0$+T. The wavelength (denoted by $\lambda_{Doppler}$) can be derived by letting the signal propagation path in FIG. 8B be equal to the propagation path in FIG. 8A as Equation (1) and (2).

$$ct_0 = c(t_0 - T) + 2v_0 T + \lambda_{Doppler} \tag{1}$$

$$\lambda_{Doppler} = T(c - 2v_0) = \lambda_0 - 2v_0 T = \lambda_0 - \Delta\lambda \tag{2}$$

where $\lambda_0 = cT$ and $\Delta\lambda = 2v_0 T$

FIGS. 8A and 8B and the above equations suggest that moving the human arm up causes a Doppler shift ($\Delta\lambda$) to a monostatic sensor configuration. This shift may cause an unexpected noise to a heart rate monitor system utilizing a Doppler shift of blood flow inside human body. It is important to note that when using a pulsed radar, the $\lambda_{Doppler}$ in Equations (1) and (2) can be considered as pulse spacing defined by propagation speed/PRF.

In addition to wearable wristband-like devices, the monostatic radar configuration could be implemented in sensor designs towards patch, armband and bed sensors for monitoring cardiovascular parameters. Use cases where data corruption from motion artifacts is not a severe issue could include implementing monostatic radar architectures in a bed, chair sensors, or seat sensors for measuring heart rate and blood pressure, similar to ballistocardiography. Individuals could be lying or seated in one position for several moments to be able to capture a continuous stream of non-degraded data. For intervals during which movement occurs such as changing positions, the data can be discarded and new streams of non-degraded data can be reacquired for continuous monitoring.

Bi-static Doppler shift is a specific example of the Doppler effect that is observed by a radar or sonar system with a separated transmitter and receiver. The Doppler shift is due to the component of motion of the object in the direction of the transmitter, plus the component of motion of the object in the direction of the receiver. Equivalently, it can be considered as proportional to the rate of change of a bistatic range.

In a bi-static radar with wavelength $\lambda$, where the distance between transmitter and target is $R_{tx}$ and distance between receiver and target is $R_{rx}$, the received bi-static Doppler frequency shift is calculated as:

$$f = \frac{1}{\lambda}\frac{d}{dt}(R_{tx} + R_{rx}) \quad (3)$$

Note that objects moving along a line connecting the transmitter and receiver can have a 0 Hz Doppler shift, as will objects moving around an ellipse of a constant bi-static range. The relationship between blood flow velocity and total cross-section area in humans is given in TABLE 1.

TABLE 1

Relation between blood flow velocity and total cross-section area in humans

| Type of Blood Vessels | Total Cross-Section Area | Blood Velocity (cm/s) |
|---|---|---|
| Aorta | 3-5 cm$^2$ | 40 cm/s |
| Capillaries | 4500-6000 cm$^2$ | 0.03 cm/s |
| Inferior and Superior Vena Cavae | 14 cm$^2$ | 15 cm/s |

Figure 9A:
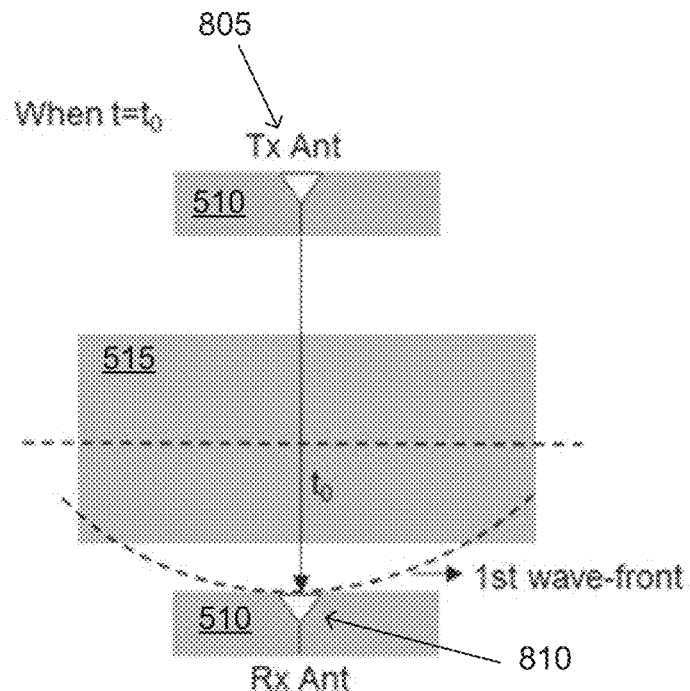
FIGS. 9A and 9B illustrate an example bi-static sensor configuration according to this disclosure.
Figure 9B:
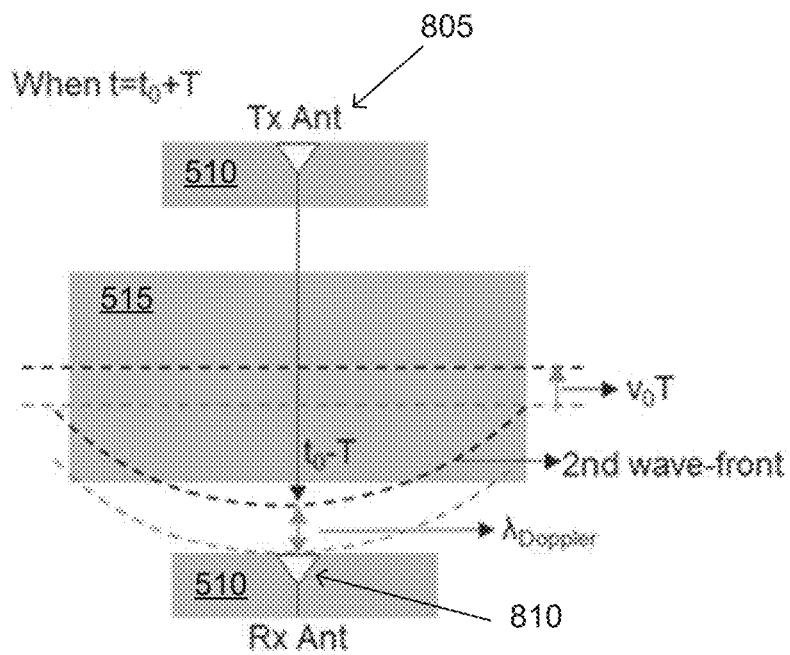

As discussed herein, a proposed sensor configuration that can be robust to Doppler shift caused by the motion of human arm can utilize a bi-static sensor configuration. The hi-static sensor configuration is positioned along a straight line that can suppress the undesired Doppler shift along that straight line. FIGS. 9A and 9B illustrate an example bi-static sensor configuration where Tx antenna 805 is positioned at the top of the wristband and Rx antenna 810 is positioned at the bottom of the wristband so that the Tx antenna 805 and the Rx antenna 810 are position 180 degrees apart from each other around the wrist 515. Equation (4) and (5) indicate that this antenna arrangement can suppress the Doppler shift related to the motion of human arm. It should be understood that by letting the signal propagation path in FIG. 9B be equal to the propagation path shown in FIG. 9A, the result will be $\lambda_{Doppler}=\lambda_0$. This suggests the hi-static configuration positioning an Rx antenna 810 on the opposite side (180 degrees from) of a Tx antenna 805 over human arm or wrist 515 cancels noise signals caused by a Doppler shift related to the motion of the human arm or wrist 515. In other words, a bi-static Tx/Rx antenna configuration as shown in FIG. 9A when $t=t_0$ (such as a first signal is transmitted from the TX antenna 805 at $t=0$ and arrives at the Rx Antenna 810 at $t=t_0$) and as shown in FIG. 9B when a second signal is transmitted at $t=T$ ($T=\lambda_0/c$ where c is light speed) and human arm or wrist 515 moves up with the velocity of $v_0$ between $t=t_0$ and $t=t_0+T$.

$$ct_0 = c(t_0-T) + \lambda_{Doppler} \quad (4)$$

$$\lambda_{Doppler} = Tc = \lambda_0 \quad (5)$$

where $\lambda_0 = cT$

In a bi-static radar setup, Tx-Rx are located in opposite directions as illustrated in FIGS. 9A and 9B. This configuration mitigates the measurement of Doppler shifts due to motion of the arm or wrist if the object moves along the line connecting the Tx antenna 805 and Rx antenna 810. Employing monostatic radar for FIRM may not be an effective approach as reflections by the skin may saturate the input amplifier. Furthermore, a Doppler shift arising from motion artifacts will easily be detected by the receive antenna. Systolic pressure can also be determined using the Doppler principle. As blood flows towards or away from the Doppler probe, the blood reflects sound waves causing a change in frequency that is detected using the same Doppler probe. Given the sensitivity of Doppler, the technique is usually reserved for the measurement of low pressures such as vascular insufficiency.

Figure 10:
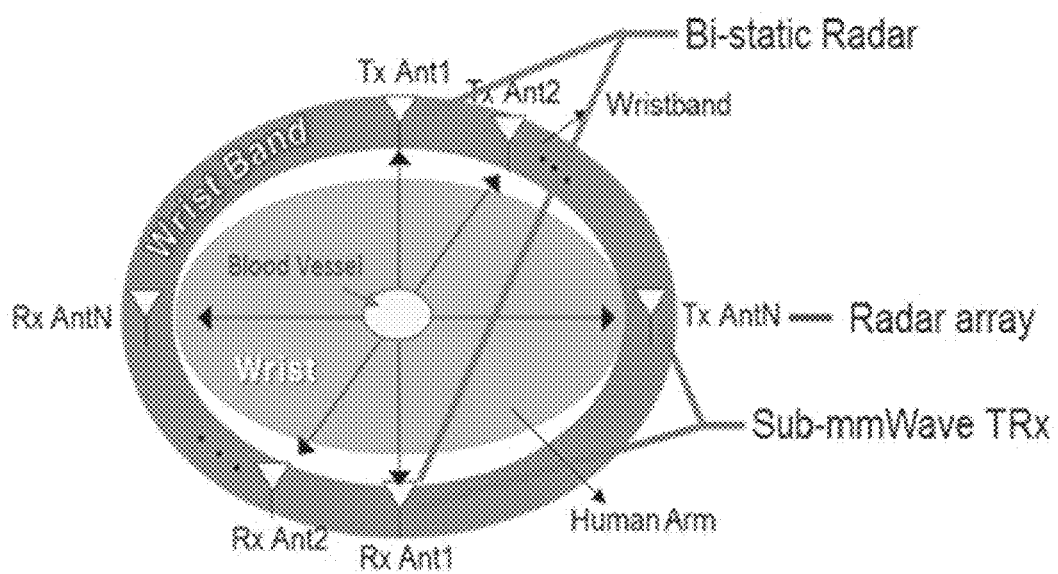
FIG. 10 illustrates an example of a non-contact HRM sensor relying on a plurality of Tx antenna and Rx antenna pairs according to this disclosure.

FIG. 10 illustrates an example of a non-contact HRM sensor relying on a plurality of Tx antenna and Rx antenna pairs according to this disclosure. The Tx antennas and Rx antenna pairs can include at least one of a bi-static radar configuration, a radar array configuration, or a sub-mmWave TRx pair. Specifications for each of the bi-static radar configuration, the radar array configuration, and the sub-mmWave TRx pair are illustrated in TABLE 2.

TABLE 2

Heart rate monitoring sensor system specifications

| Categories | Sub-categories | Value |
|---|---|---|
| System Configuration (Wrist watch form factor) | Number of array | >2 (perpendicular) |
| | Distance between TRx | 5~7 cm |
| TRx Specifications Link Budget | Carrier Frequency | ~24 GHz (factoring SAR) |
| | Transmitted Power | 0 dBm |
| | Channel loss | 60 dB |
| | Antenna gain | 4 dB (2 dB on both Tx and Rx sides) |
| | Rx sensitivity | −80 dBm |
| | SNR | 24 dB |

TABLE 2-continued

Heart rate monitoring sensor system specifications

| Categories | Sub-categories | Value |
|---|---|---|
| Power Breakdown | VCO | 8 mW |
| | PA | 8 mW |
| | LNA | 8 mW |
| | Mixer | No $P_{DC}$ (passive) |
| | Other front-end I/O | 6 mW |

In an embodiment, bi-static radar configuration includes a situation where no Doppler shift is recorded due to motion when the object moves along a path between aTx antenna and a Rx antenna. The signal loss is half of the signal loss of a monostatic radar which is not immune to motion degradation. In an embodiment, a radar array configuration can be employed for multi-dimensional motion cancellation. In an embodiment, a sub mmWave TRx antennas utilizing low power Tx antennas, a highly sensitive on-body antenna and high-resolution using sub-millimeter waves (10~100 GHz). Pulse-Doppler radar is based on the Doppler Effect, where movement in range produces a frequency shift on the signal reflected from the target.

$$\text{Doppler Frequency} = \left( \frac{2 \times \text{Transmit Frequency} \times \text{Range Velocity}}{C} \right) \quad (6)$$

Radial velocity can be used for pulse-Doppler radar operation. As the reflector moves between each transmit pulse, the returned signal has a phase difference or phase shift from pulse to pulse. This phase shift causes the reflector to produce a Doppler modulation on the reflected signal. Pulse-Doppler radars exploit this phenomenon to improve performance. The amplitude of the successively returning pulse from the same scanned volume is:

$$I = I_0 \sin\left( \frac{4\pi(x_0 + v\Delta t)}{\lambda} \right) = I_0 \sin(\Theta_0 + \Delta\Theta) \quad (7)$$

where, $x_0$ is the distance radar to the target, $\lambda$ is the radar wavelength and $\Delta t$ is the time between two pulses. So, $$\Delta\Theta = \left( \frac{4\pi v \Delta t}{\lambda} \right) \quad (8)$$

This allows the radar to separate the reflections from multiple objects located in the same volume of space by separating the objects using a spread spectrum to segregate different signals.

$$v = \text{target speed} = \frac{\lambda \Delta \Theta}{4\pi \Delta t} \quad (9)$$

where $\Delta\Theta$ is the phase shift induced by range motion. The desired precision would range from 1-5 cm/s.

The bi-static radar architecture can be used for mobile and wearable devices involving a range of limb movement. This can help mitigate motion artifacts and generate unperturbed continuous streams of data for yielding reliable cardiovascular parameters. Such devices would entail wristbands and armbands where the propensity for subject motion is high, for example, during physical fitness activities.

As discussed herein, a sensor can detect velocity of arterial blood flow in the human wrist. The two major arteries in the wrist are the radial and the ulnar arteries. The physical properties of both these vessels are shown in TABLE 3.

TABLE 3

Physical Properties of Arteries in the Wrist

| Arteries | Mean Diameter (cm) | Radius (cm) | Cross-sectional area (cm$^2$) | Length (cm) |
|---|---|---|---|---|
| Radial | 0.254 | 0.127 | 0.0507 | 18.1 |
| Ulnar | 0.212 | 0.106 | 0.0353 | 18.5 |

On the basis of the Poiseuille-Hagen formula for flow rates given by equation 10, the average arterial blood flow velocities can be calculated using equation 11. These velocities for the radial and ulnar arteries are shown in TABLE 4.

$$\text{Flow} = \Delta_p \frac{\pi}{8} \times \frac{1}{n} \times \frac{r^4}{L} \quad (10)$$

where $\Delta_p$ is the pressure difference or mean pressure in pascals, $\eta$ is the viscosity in Poise, and r and L are the radius and length of the vessel.

$$V_{avg} = \frac{\text{Flow}}{\text{Cross-Sectional Area}} \quad (11)$$

TABLE 4

Average velocity or arterial flow in the Wrist

| Arteries | Viscosity (Poise) | Pressure diff (mean pressure) (mm Hg) | Pressure diff (Pa) | Flow (mL or cc/s) | Average Velocity (cm/s) |
|---|---|---|---|---|---|
| Radial | 0.0524 | 80 | 10664 | 1.14806 | 22.64815 |
| Ulnar | 0.0524 | 80 | 10664 | 0.54511 | 15.43632 |

If arterial blood flow radial velocities are to be assumed to range between 5 cm/s and 60 cm/s, Doppler frequencies for potential ultra-wide band operational frequencies of 3.1 GHz, 10 GHz and 24 GHz frequencies can be calculated as illustrated in TABLE 5.

TABLE 5

Doppler frequencies for arterial blood flow radial velocity

| Transmitted Frequency (GHz) | Minimum Doppler Frequency (Hz) | Maximum Doppler Frequency (Hz) |
|---|---|---|
| 3.1 | 1.03 | 12.4 |
| 10.0 | 3.34 | 40.0 |
| 24.0 | 8.0 | 96.0 |

Accordingly, the influence of the angle on the Doppler frequency for average velocity determined in TABLE 4 is illustrated in TABLE 6.

TABLE 6

Doppler frequencies for average arterial blood flow radial velocity vs. angle

| Angle (Deg) | Radial Doppler Freq @ 3.1 GHz TX (Hz) | Ulnar Doppler Freq @ 3.1 GHz TX (Hz) | Radial Doppler Freq @ 10 GHz TX (Hz) | Ulnar Doppler Freq @ 10 GHz TX (Hz) | Radial Doppler Freq @ 24 GHz TX (Hz) | Ulnar Doppler Freq @ 24 GHz TX (Hz) |
|---|---|---|---|---|---|---|
| 0 | 4.812435 | 3.280016 | 15.52398 | 10.5807 | 37.25756 | 25.29704 |
| 10 | 4.739323 | 3.230185 | 15.28814 | 10.41995 | 36.69153 | 24.5284 |
| 20 | 4.522209 | 3.082207 | 14.58777 | 9.942603 | 35.01065 | 23.01448 |
| 30 | 4.167691 | 2.840577 | 13.44416 | 9.163152 | 32.26599 | 20.80128 |
| 40 | 3.686539 | 2.512638 | 11.89206 | 8.105284 | 28.54094 | 17.95604 |
| 50 | 3.093373 | 2.108354 | 9.978624 | 6.801141 | 23.9487 | 14.56521 |
| 60 | 2.406217 | 1.640008 | 7.761991 | 5.290348 | 18.62378 | 10.73183 |
| 70 | 1.64595 | 1.121832 | 5.309515 | 3.618811 | 12.74284 | 6.572366 |
| 80 | 0.83567 | 0.569569 | 2.695711 | 1.837319 | 6.469707 | 2.213204 |
| 90 | 2.95E−16 | 2.01E−16 | 9.51E−16 | 6.48E−16 | 2.28E−15 | 25.39367 |

For system considerations entailing RF channel loss analysis, a 6-layer or component model of the human wrist is being considered to effectively calculate the RF channel loss through tissue at three UWB frequencies of 3.1 GHz, 10 GHz and 24 GHz. The components consist of bone (marrow), blood, nerve, muscle, fat and skin (dry). TABLE 7 provides the mass densities and thicknesses of each layer of the model under consideration.

TABLE 7

Wrist tissue mass density and thickness for a 6-layer model

| Layer | Mass density (Kg/m³) | Thickness (m) |
|---|---|---|
| Bone (marrow) | 1908 | 0.017 |
| Blood | 1050 | 0.004 |
| Nerve | 1075 | 0.001 |
| Muscle | 1090 | 0.015 |
| Fat | 911 | 0.0015 |
| Skin (dry) | 1109 | 0.0015 |

The dielectric properties reflecting conductivity (σ, S/m), relative permittivity ($\in_r$), loss tangent ($\delta_e$), wavelength (λ, m) and penetration depth for each of the 6 components in the wrist model were determined as illustrated in TABLE 8.

It is expected that because the characteristic impedances of various tissues or layers inside the wrist model are different, there will be partial reflection of the electromagnetic energy radiated at the interface between various media. For this reason, a frequency dependent model (separately for 3.1 GHz, 10 GHz and 24 GHz) was developed. The overall loss will take into account the channel path loss, the attenuation in tissues and losses due to the reflections at the interface between tissues. The dielectric properties shown in TABLE 8 along with certain assumed RF system parameters have been considered for calculating path loss. Further, since the device is anticipated to be placed on the human wrist, near field equations have been used in order to estimate the path loss. The path loss (PL) was estimated as given by:

$$PL(f) = \frac{P_{Tx}G_{Tx}G_{Rx}}{4} \times \left[ \left(\frac{\lambda}{4\pi d}\right)^2 - \left(\frac{\lambda}{4\pi d}\right)^4 + \left(\frac{\lambda}{4\pi d}\right)^6 \right] \quad (12)$$

where f is the frequency, $P_{Tx}$ is the transmit power (max=−10.5 dBm), $G_{Tx}$ and $G_{Rx}$ are the antenna transmit (10 dB) and receive gain (10 dB) values, λ is the tissue wavelength and d is the distance between the transmit and receive antennae (0.05 m).

TABLE 8

Wrist tissue dielectric properties fr 6-layer model at 3.1 GHz, 10 GHz and 24 GHz

| Layer | σ (S/m) | | | $\epsilon_r$ | | | Tan $\delta_e$ | | | λ (m) | | | Penetration depth (m) | | |
|---|---|---|---|---|---|---|---|---|---|---|---|---|---|---|---|
| | 3.1 GHz | 10.0 GHz | 24.0 GHz | 3.1 GHz | 10.0 GHz | 24.0 GHz | 3.1 GHz | 10.0 GHz | 24.0 GHz | 3.1 GHz | 10.0 GHz | 24.0 GHz | 3.1 GHz | 10.0 GHz | 24.0 GHz |
| Bone marrow | 0.126 | 0.578 | 1.483 | 5.227 | 4.607 | 3.538 | 0.140 | 0.225 | 0.289 | 0.042 | 0.014 | 0.006 | 0.097 | 0.020 | 0.007 |
| Blood | 3.149 | 13.131 | 32.951 | 57.187 | 45.109 | 27.077 | 0.319 | 0.523 | 0.911 | 0.013 | 0.004 | 0.002 | 0.013 | 0.003 | 0.001 |
| Nerve | 1.377 | 6.030 | 15.554 | 29.529 | 23.778 | 15.370 | 0.270 | 0.456 | 0.758 | 0.018 | 0.006 | 0.003 | 0.021 | 0.004 | 0.001 |
| Muscle | 2.322 | 10.626 | 29.437 | 51.936 | 42.764 | 37.395 | 0.248 | 0.447 | 0.805 | 0.013 | 0.004 | 0.002 | 0.017 | 0.003 | 0.001 |
| Fat | 0.135 | 0.583 | 1.489 | 5.214 | 4.602 | 3.836 | 0.150 | 0.229 | 0.291 | 0.042 | 0.014 | 0.006 | 0.090 | 0.020 | 0.007 |
| Skin (dry) | 1.795 | 5.014 | 22.841 | 37.358 | 31.290 | 18.993 | 0.279 | 0.460 | 0.901 | 0.016 | 0.005 | 0.003 | 0.018 | 0.004 | 0.001 |

The preliminary path loss calculations for the 6-layer model at all three UWB frequencies are illustrated in TABLE 9.

TABLE 9

Path Loss estimates for 6-layer wrist model at 3.1 GHz, 10 GHz and 24 GHz

| Layer | Path Loss 3.1 GHz (dB) | Path Loss 10.0 GHz (dB) | Path Loss 24.0 GHz (dB) |
|---|---|---|---|
| Whole arm (average) | −50.321 | −59.881 | −66.343 |
| Bone (marrow) | −45.401 | −55.059 | −61.904 |
| Blood | −55.877 | −65.184 | −71.007 |
| Nerve | −52.977 | −62.342 | −68.362 |
| Muscle | −55.417 | −64.883 | −70.927 |
| Fat | −45.393 | −55.056 | −61.903 |
| Skin (dry) | −54.003 | −63.538 | −69.453 |

A preliminary evaluation of the attenuation (Att) at each wrist layer has been performed and is illustrated in TABLE 10 given by:

$$Att(f) = \Pi_{i=0}^{7} \exp\left(-\frac{2d_i}{\delta_i}\right) \quad (13)$$

where $d_i$ and $\delta_i$ are the thickness and penetration depth, respectively, of each $i^{th}$ tissue in the model.

TABLE 10

Attenuation values for 6-layer wrist model

| Layer | 3.1 GHz | 10.0 GHz | 24.0 GHz |
|---|---|---|---|
| Whole arm (average) | 0.6770 | 0.1557 | 0.0139 |
| Bone (marrow) | 0.7035 | 0.1802 | 0.0082 |
| Blood | 0.5380 | 0.0575 | 0.0002 |
| Nerve | 0.9097 | 0.6346 | 0.2447 |
| Muscle | 0.1775 | 0.0001 | $1.0 \times 10^{-13}$ |
| Fat | 0.9672 | 0.8580 | 0.6536 |
| Skin (dry) | 0.8484 | 0.4539 | 0.0649 |

In both equations 12 and 13, losses in the path from the radar to a layer and a reverse path from the layer back to the radar have been taken into account. A comprehensive lab bench setup was undertaken using a commercially available ultra-wideband (UWB) radar module (3-10 GHz) and a peristaltic pump system (such as Cole Parmer) to measure flow velocities of a blood-like fluid pumped across a tube that was placed inside a 3-D printed phantom mimicking the human wrist. The impulse UWB radar module used the following parameters: Center frequency, 7.3 GHz; bandwidth, 2.35 GHz; pulse rate repetition, 100 MHz; RF sample rate, 39.96 GHz and frame rate of 77.7 Hz.

Figure 11A:
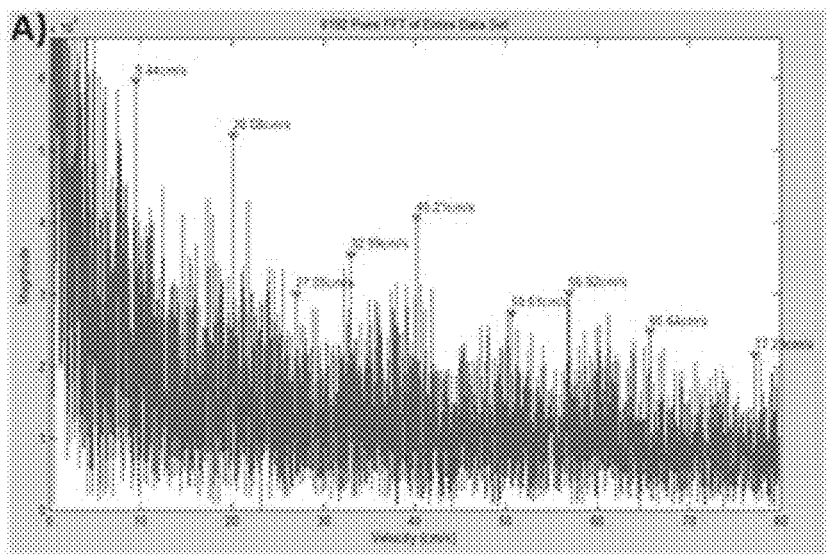
FIGS. 11A and 11B illustrate example charts of measured velocities according to this disclosure.
Figure 11B:
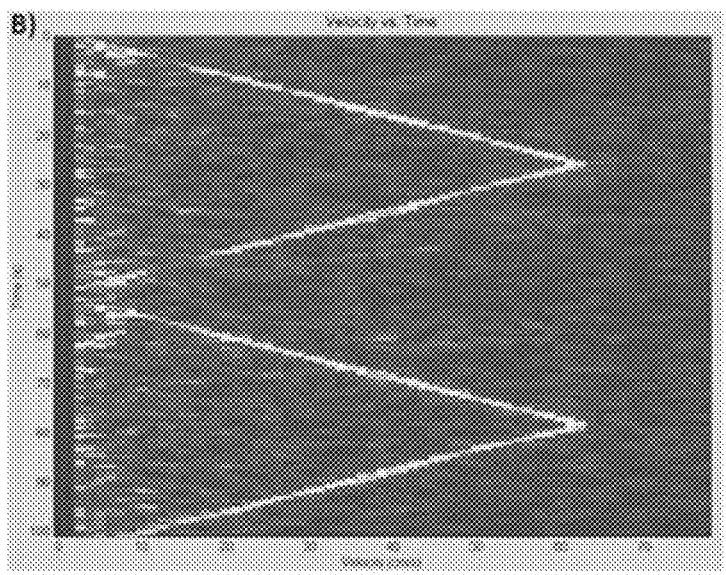

FIGS. 11A and 11B illustrate example charts of measured velocities as a result of the comprehensive lab bench setup according to this disclosure. FIGS. 11A and 11B illustrate the feasibility of obtaining a linear velocity sweep of 5 to 62 cm/s with a setup mimicking human blood flow in a vessel such as the radial artery. By computing the blood flow velocities and using the pulse wave velocity and pulse transit time equations, an estimate of the mean end point blood pressure can be obtained. FIG. 11A plots velocity versus magnitude and FIG. 11B plots velocity versus time. FIGS. 11A and 11B illustrate the characterization of various speed components in the flow following a linear velocity sweep from 5 cm/s to 62 cm/s.

By employing a sequence of signal processing and intelligence algorithm chains, blood pressure can be inferred continuously by employing either monostatic or bistatic radar architectures for mobile form factors. EM Doppler effects can be captured at a single point and do not require tight contact nor the advance skin preparation that is a mainstay of current oscillometric blood pressure measurement methods.

Previously, the Poiseuille-Hagen relationship for flow pressure being linearly proportional to flow speed was described in Equation 10. In biological systems, however, the relationship is nonlinear. The biological tube, such as an artery, is elastic with changing size, and has multiple branches with complicated fluid dynamics. Also, the blood pressure of interest is the mean arterial pressure, where the difference of blood pressure alone does not give a complete picture. Nonetheless, regression models correlate blood flow and arterial blood pressure, where the blood flow is measured invasively by inserting sensing probes into the artery.

Figure 12:
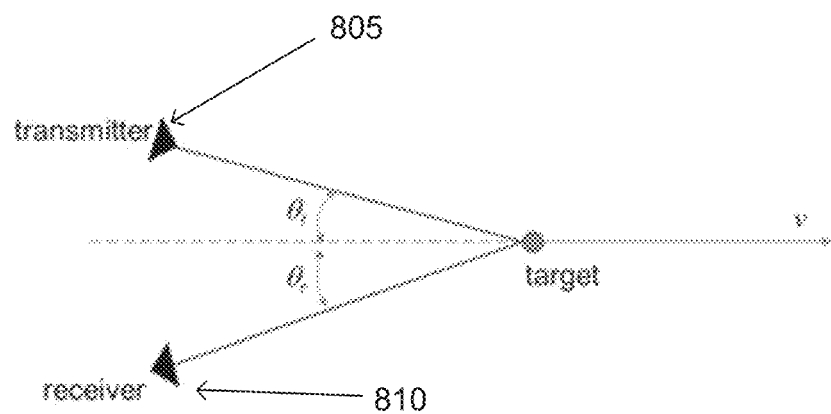
FIG. 12 is an example diagram of measuring speed of a single moving target according to this disclosure.

FIG. 12 is an example diagram of measuring speed of a single moving target according to this disclosure. As shown in FIG. 12, the Doppler effect can be utilized to measure the speed of a moving object, where the Doppler frequency for a fixed source when v<<c is given by:

$$f_d = -\frac{f_s v}{c}(\cos\theta_t + \cos\theta_r) \quad (14)$$

where $f_s$ is the source frequency, of a continuous wave system, and c is the speed of the Doppler source which can be the speed of light if an electromagnetic wave is generated, or the speed of sound if a sound wave is generated. $\theta_t$ and $\theta_r$ are the angles formed with the target from the transmitter and receiver, respectively. By observing the Doppler frequency $f_d$, the velocity of the target can be obtained.

Figure 13:
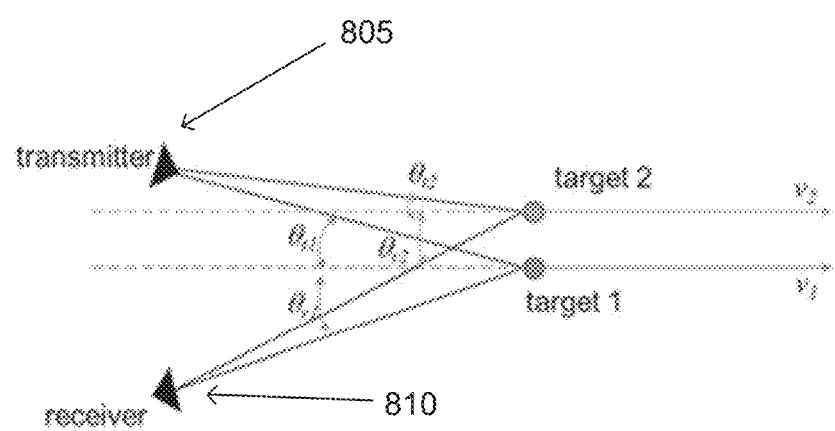
FIG. 13 illustrates an example diagram of mixed Doppler effects according to this disclosure.

FIG. 13 illustrates an example diagram of mixed Doppler effects according to this disclosure. Mixed Doppler effects are measured in multiple target cases. As shown in FIG. 13, when measuring speed related information pertaining to a stream of flow containing multiple particles, the resulting measurement is not flow speed, but a weighted average of Doppler frequencies, depending on target speed, angular differences, and reflectance. In the pulsed wave system, equation (2) is modified to use phase information to recover velocity. In the case of multiple targets, a weighted average of phases is measured and used to obtain velocity. EM waves of visible light wavelength can be used, or RF for deeper penetration through tissues surrounding an embedded artery can be used. Also, continuous wave, pulsed wave, or both can be used.

Figure 14:
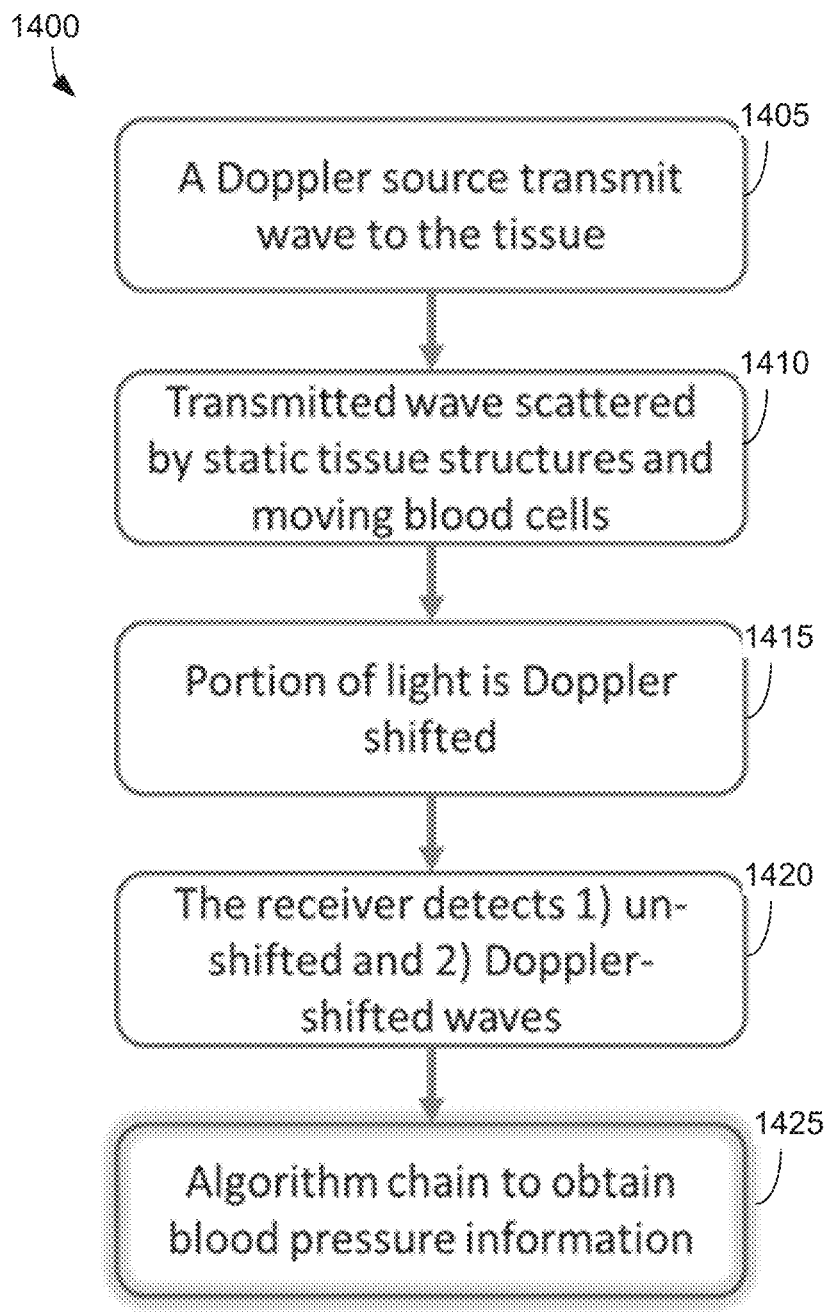
FIG. 14 illustrates an example method to obtain Doppler information according to this disclosure.

FIG. 14 illustrates an example method 1400 to obtain Doppler information according to this disclosure. At step 1405, a device, using a transmit antenna, transmits a Doppler source transmit wave to a target (such as tissue). At step 1410, the transmitted wave is scattered by static tissue structures and moving blood vessels. At step 1415, a portion of light is Doppler shifted. At step 1420, the device receives, using a receive antenna, and detects un-shifted waves and Doppler shifted waves. At step 1425, the device, using a processor, implements an algorithm chain to obtain blood pressure information. For example, information about blood pressure is obtained through a sequence of signal processing steps and intelligent algorithm components. The Doppler source can either be narrowband or broadband. The bandwidth and frequency depends on the manufactural and computational cost for the target product, where broadband sources have lower manufactural cost while narrowband devices reduce signal processing complexity. The mixture of both narrowband and broadband can be utilized.

FIGS. 15A, 15B, and 15C illustrate example graphs to show how heart rate is calculated according to this disclosure. FIG. 15A illustrates an example graphs before baseline wandering 1505 and after baseline wandering is removed 1510. FIG. 15B illustrates an example graph that identifies peaks corresponding to contractions of the heart. FIG. 15C illustrates an example graph of a Doppler heart beat 1515 compared to a standard heart beat 1520. The weighted average of velocity, or simply velocity from now on, is obtained continuously based on the Doppler principle from the receiver data, such as equation (14) for the continuous wave case. In the case of pulsed Doppler systems, the velocity can also be obtained in a similar way based on the phase shift information from pulse to pulse. The extracted velocity time series is shown as blue curves 1505 in FIG. 15A.

Once the continuous time series velocity is obtained, it undergoes filtering to remove baseline wandering and noise, resulting in the red curve 1510 shown in FIG. 15A. Following that, the filtered velocity time series is segmented into heartbeat cycles based on the peaks and valleys induced as the blood flows faster when the heart squeezes as shown in FIG. 15B. Finally the segments are windowed, resulting in the Doppler heartbeats where the end points are zero at the curve 1515 in FIG. 15C.

Based on each Doppler heartbeat, a number of features are computed. The goal of computing the features are to transform the Doppler heartbeat into spaces where information corresponding to blood pressure is easy to extract, and the Doppler heartbeat can be represented in a lower dimension, hence the complexity and RAM requirements are reduced. For sparse representation feature, the Doppler heartbeat can be represented in a much lower dimension than the n samples in the original time series. For example, in the Fourier or Wavelet domain, where the largest k components exist, k<<n. For moments, each representation usually has physical or mathematical meaning, for example frequency, spatiotemporal location, time/phase shifts and so on which collectively we refer to as semantic quantities. Moments are the coefficient of the representation of the Doppler heartbeat times the semantics. For example, an n-th moment in Fourier space is:

$$M_n = \int_{-\infty}^{+\infty} \omega^n S(\omega) d\omega \qquad (15)$$

where $S(\omega)$ is the frequency spectrum and $\omega$ is the frequency. Note that the moment n can be non-integer also. Usually the corresponding n-th root will be taken to normalize the results, while different normalization can also be taken as discussed later in the inference part.

For moment ratios, the ratio of moments from equation (15) can also be used as features. Further, by taking the log of the ratios, the result is proportional to the amplitude difference in dB among moments which is an alternative form of moment ratios that can be used, especially if the ratios differ significantly. For mixture waveform representations, the Doppler heartbeat can also be represented by a mixture of waveforms. An example family of waveforms for mixture representation is the exponential family which includes Gaussians. By mixture it may involve the sum of different scaled versions of the waveforms that are shifted in time. The family of such representation can also be learned empirically based on training data.

The computed features of each heartbeat are fed into a sequence of inference algorithms to infer blood pressure. The first layer of an inference algorithm takes the feature directly as the input and outputs information related to blood pressure. The following layers take inputs from previous layers, and further distil blood pressure, until the last layer which outputs blood pressure is estimated.

Figure 16:
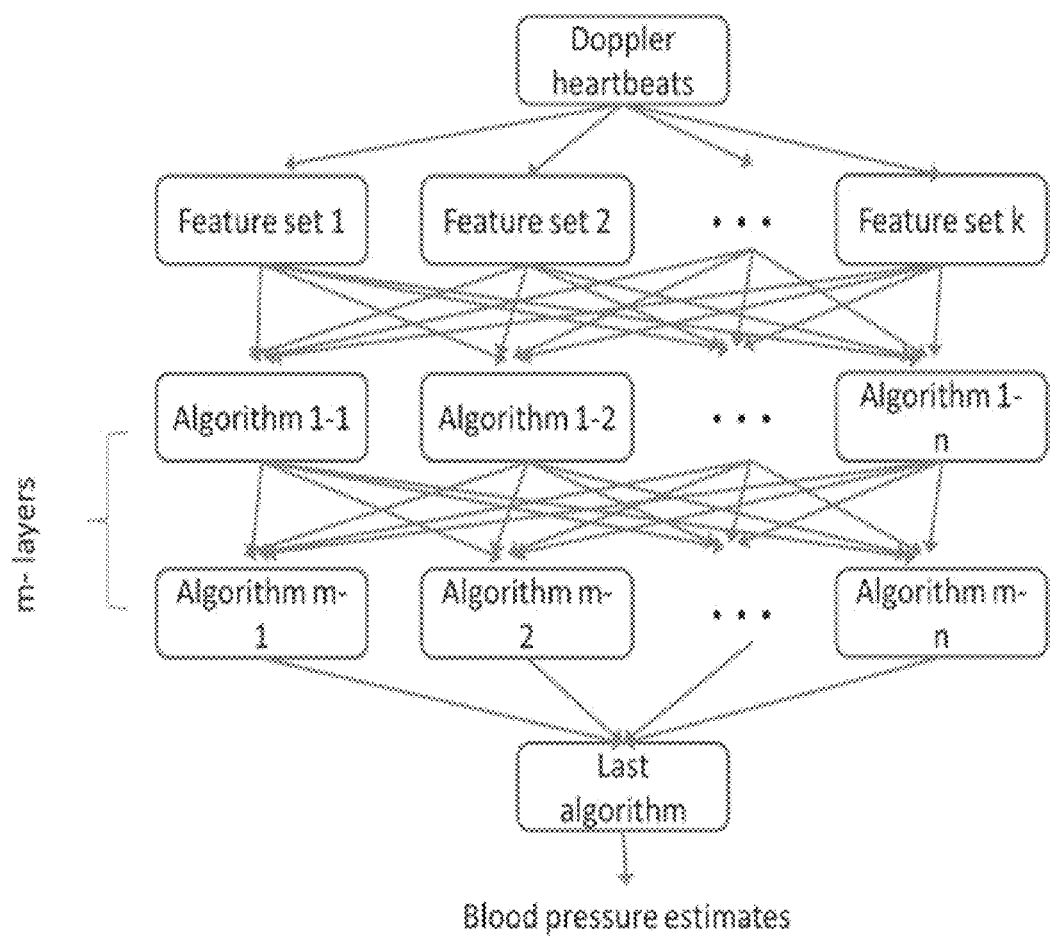
FIG. 16 illustrates an example blood pressure estimation algorithm chain according to this disclosure.

FIG. 16 illustrates an example blood pressure estimation algorithm chain according to this disclosure. Blood pressure estimation algorithm chain that includes features that are computed from the Doppler heartbeats followed by m-layers of algorithms to extract blood pressure information for the last algorithm are used to output blood pressure estimates. The sets of algorithms used at each layer can be of various complexities, or even remain the same algorithm. The design and algorithm choice are related to the architecture in the form.

The algorithms used at each layer can be simple artificial neurons, and the neurons at each layers aim to output their own estimates of blood pressure, while the subsequent layer of neurons aggregate the estimates to form a committee of estimates such that the estimates from the last layer are used as the final estimates. The algorithm used at each layer can be simple artificial neurons, while each layer aims to extract information from the previous layer for an efficient representation, and only the last (few) layers estimate the blood pressure based on the hierarchical representation results. This corresponds to deep learning. The algorithm used at each layer being other regression algorithm, such as logistic or support vector machines (SVM), where each algorithm outputs its own estimate of blood pressure, and the last layer outputs the final estimates. The algorithms used at each layer are sparse representation algorithms, except the last (few) layers, which output the final estimates of blood pressure. The algorithms can be a mixture of design points discussed herein, where some components in some layers perform one of the following: sparse representation, dimensionality reduction, BP information extraction, and final estimation of blood pressure.

The parameters of the inference algorithm and architecture of the algorithm sequence are tuned based on standard training, testing, and validation procedures, or also known as calibration, using blood pressure reading from a reference device such as an oscillometric device or human experts utilizing stethoscopes and cuffs. The algorithm tuning and calibration is done once, prior to deployment to the end consumer. A refined calibration mode is also available such that extra reference blood pressure measurements together with the Doppler signal measured by aforementioned embodiments are used to further tune and customize for individual implementations.

The performance results from the experimental studies that were conducted are shown in TABLE 11. The error is measured in absolute difference compared to a reference signal.

TABLE 11

Blood pressure estimation performance based on this invention

| Subject | Stand, arm relax | | Sit, induced higher BP, arm relax | | Sit, recover from higher BP, arm relax | |
|---|---|---|---|---|---|---|
| | Systolic | Diastolic | Systolic | Diastolic | Systolic | Diastolic |
| 1 | 5.76 | 3.24 | 5.36 | 2.75 | 4.67 | 4.09 |
| 2 | 6.59 | 4.56 | 8.3 | 4.88 | 6.24 | 3.28 |

TABLE 11-continued

Blood pressure estimation performance based on this invention

| | Stand, arm relax | | Sit, induced higher BP, arm relax | | Sit, recover from higher BP, arm relax | |
|---|---|---|---|---|---|---|
| Subject | Systolic | Diastolic | Systolic | Diastolic | Systolic | Diastolic |
| 3 | 4.23 | 4.74 | 5.59 | 7.16 | 5.07 | 3.73 |
| 4 | 4.55 | 6 | 4.36 | 5.93 | 3.69 | 4.09 |
| Avg. | 5.28 | 4.63 | 5.91 | 5.18 | 4.92 | 3.80 |

The algorithms proposed herein can be applied to monostatic and bi-static Doppler architecture platforms for measuring real-time and continuous blood pressure without the use of a cuff and while using a single sensing location. It further affords convenience through measurements made during natural and normal skin contact and can be optimized to enable low computational and memory complexity to be deployable in mobile and wearable devices.

Figure 17:
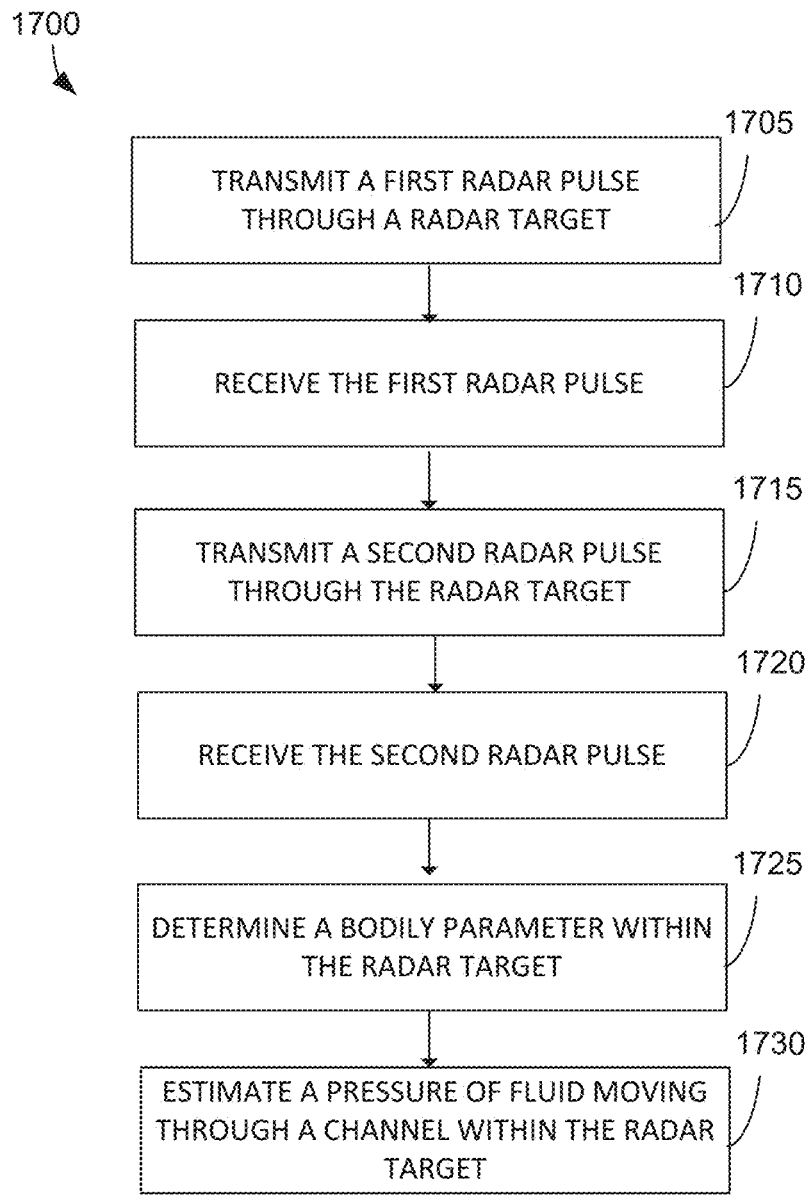
FIG. 17 illustrates an example method to measure a bodily parameter according to this disclosure.

FIG. 17 illustrates an example method 1700 to measure a bodily parameter according to this disclosure. At step 1705, a device transmits, using a transmit (Tx) antenna of an antenna pair, a first radar pulse to a receive (Rx) antenna of the antenna pair. At step 1710, the device receives, using the Rx antenna, the first radar pulse. The first radar pulse travels through a radar target between the Tx antenna and the Rx antenna. At step 1715, the device transmits, using the Tx antenna, a second radar pulse to the Rx antenna. At step 1720, the device receives, using the Rx antenna, the second radar pulse. The second radar pulse travels through the radar target between the Tx antenna and the Rx antenna. At step 1725, the device, using a processor, determines a bodily parameter within the radar target as a function of the transmission and the reception of the first radar pulse and the second radar pulse. At step 1730, the device, using the processor, estimates a pressure of a fluid within a channel of the radar target as a function of at least one of a fluid velocity of the fluid travelling through the channel or the cross-sectional area of the channel.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A device to measure a bodily parameter, the device comprising:
a first antenna pair including a first transmit (Tx) antenna configured to transmit one or more radar pulses and a first receive (Rx) antenna configured to receive the one or more radar pulses, wherein the first Tx antenna and the first Rx antenna are positioned so that a radar target can be positioned on a first straight line between the first Tx antenna and the first Rx antenna;
a second antenna pair including a second transmit (Tx) antenna configured to transmit one or more radar pulses and a second receive (Rx) antenna configured to receive the one or more radar pulses, wherein the second Tx antenna and the second Rx antenna are positioned so that a radar target can be positioned on a second straight line between the second Tx antenna and the second Rx antenna, wherein the second antenna pair are positioned so that one or more radar pulses transmitted from the second transmit antenna reach the radar target at an angle relative to the one or more radar pulses transmitted from the first transmit antenna;
wherein the first antenna pair and the second antenna pair are positioned relative to each other to mitigate motion artifacts; and
a processor configured to:
control the first and second Tx antennas to transmit a first radar pulse and a second radar pulse,
control the first and second Rx antennas to receive the first radar pulse and the second radar pulse, wherein the first radar pulse and the second radar pulse travel through the radar target, and
determine a bodily parameter within the radar target as a function of the transmission and the reception of the first radar pulse and the second radar pulse between each of the first and second antenna pairs.

2. The device of claim 1, wherein the processor is configured to determine the bodily parameter within the radar target by detecting a phase shift between the received first radar pulse and the received second radar pulse.

3. The device of claim 1, wherein the processor is further configured to estimate a pressure of a fluid within a channel as a function of at least one of a fluid velocity of the fluid travelling through the channel or a cross-sectional area of the channel.

4. The device of claim 1, wherein the second antenna pair are positioned so that one or more radar pulses transmitted from the second transmit antenna reach the radar target orthogonally relative to the one or more radar pulses transmitted from the first transmit antenna.

5. The device of claim 1, wherein the second antenna pair are sub-mmWave antennas.

6. The device of claim 1, further comprising:
a third antenna pair including a third transmit (Tx) antenna configured to transmit one or more radar pulses and a third receive (Rx) antenna configured to receive the one or more radar pulses, wherein the third Tx antenna and the third Rx antenna are positioned so that a radar target can be positioned between the third Tx antenna and the third Rx antenna.

7. The device of claim 1, wherein the device comprises at least one of a wristwatch, an armband, a torso-band, or one or more patches.

8. A method implemented by a device to measure a bodily parameter, the method comprising:
transmitting, by a first transmit (Tx) antenna of a first antenna pair, a first radar pulse to a first receive (Rx) antenna of the first antenna pair;
receiving, by the first receive (Rx) antenna of the first antenna pair, the first radar pulse, wherein the first radar pulse travels through a radar target on a first straight line between the first Tx antenna and the first Rx antenna;
transmitting, by the first Tx antenna, a second radar pulse to the first Rx antenna;
receiving, by the first Rx antenna, the second radar pulse, wherein the second radar pulse travels through the radar target on the first straight line between the first Tx antenna and the first Rx antenna;
positioning a second antenna pair relative to the first antenna pair at an angle to mitigate motion artifacts;
transmitting, by a second transmit (Tx) antenna of the first antenna pair, a first radar pulse to a second receive (Rx) antenna of the second antenna pair;
receiving, by the second receive (Rx) antenna of the second antenna pair, the first radar pulse, wherein the first radar pulse travels through the radar target on a second straight line between the second Tx antenna and the second Rx antenna;

transmitting, by the second Tx antenna, a second radar pulse to the second Rx antenna;

receiving, by the second Rx antenna, the second radar pulse, wherein the second radar pulse travels through the radar target on the second straight line between the second Tx antenna and the second Rx antenna, wherein the second antenna pair are positioned so that one or more radar pulses transmitted from the second transmit antenna reach the radar target at an angle relative to the one or more radar pulses transmitted from the first transmit antenna;

determining a bodily parameter within the radar target as a function of the transmission and the reception of the first radar pulse and the second radar pulse between each of the first and second antenna pairs, wherein the first radar pulse and the second radar pulse comprise a Doppler radar pulse.

9. The method of claim 8, wherein determining a bodily parameter comprises detecting a phase shift between the received first radar pulse and the received second radar pulse.

10. The method of claim 8, further comprising estimating a pressure of a fluid within a channel as a function of at least one of a fluid velocity of the fluid travelling through the channel or a cross-sectional area of the channel.

11. The method of claim 8, wherein the device comprises at least one of a wristwatch, an armband, a torso-band, or one or more patches.

12. The method of claim 8, wherein the second antenna pair are positioned so that one or more radar pulses transmitted from the second transmit antenna reach the radar target at an orthogonal angle relative to the one or more radar pulses transmitted from the first transmit antenna.

* * * * *